United States Patent [19]

Ullman et al.

[11] Patent Number: 5,340,716

[45] Date of Patent: Aug. 23, 1994

[54] ASSAY METHOD UTILIZING PHOTOACTIVATED CHEMILUMINESCENT LABEL

[75] Inventors: Edwin F. Ullman, Atherton; Hrair Kirakossian, San Jose; John S. Pease, Los Altos; Yuri Daniloff, Mountain View; Daniel B. Wagner, Sunnyvale, all of Calif.

[73] Assignee: Snytex (U.S.A.) Inc., Palo Alto, Calif.

[21] Appl. No.: 718,490

[22] Filed: Jun. 20, 1991

[51] Int. Cl.$^5$ .............................................. C12Q 1/00
[52] U.S. Cl. .......................................... 435/6; 435/77
[58] Field of Search ................ 435/5, 6, 7.92, 125, 435/7.7; 436/501

[56] References Cited

U.S. PATENT DOCUMENTS

| | | | |
|---|---|---|---|
| 3,850,578 | 11/1974 | McConnell | 23/230 |
| 3,996,345 | 12/1976 | Ullman et al. | 424/12 |
| 4,174,384 | 11/1979 | Ullman et al. | 424/8 |
| 4,193,983 | 3/1980 | Ullman et al. | 424/12 |
| 4,199,559 | 4/1980 | Ullman et al. | 424/8 |
| 4,220,450 | 9/1980 | Maggio | 23/230 |
| 4,226,993 | 10/1980 | Buckler et al. | 544/237 |
| 4,233,402 | 11/1980 | Magggio et al. | 435/7 |
| 4,261,968 | 4/1981 | Ullman et al. | 424/8 |
| 4,277,437 | 7/1981 | Maggio | 422/61 |
| 4,299,916 | 11/1981 | Litman et al. | 435/6 |
| 4,311,712 | 1/1982 | Evans et al. | 424/365 |
| 4,315,998 | 2/1982 | Neckers et al. | 525/332 |
| 4,318,707 | 3/1982 | Litman et al. | 23/230 B |
| 4,380,580 | 4/1983 | Boguslaski et al. | 435/7 |
| 4,383,031 | 5/1983 | Bugslaski et al. | 435/7 |
| 4,483,921 | 11/1984 | Cole | 435/7 |
| 4,483,929 | 11/1984 | Szoka | 435/533 |
| 4,485,054 | 11/1984 | Mezei et al. | 264/4.6 |
| 4,522,803 | 6/1985 | Lenk et al. | 424/1.1 |
| 4,529,561 | 7/1985 | Hunt et al. | 264/4.3 |
| 4,576,912 | 3/1986 | Yaverbaum et al. | 435/7 |
| 4,588,578 | 5/1986 | Fountain et al. | 424/1.1 |
| 4,650,770 | 3/1987 | Liu et al. | 436/523 |
| 4,652,533 | 3/1987 | Tolley | 436/518 |
| 4,654,300 | 3/1987 | Zuk et al. | 435/7 |
| 4,891,324 | 1/1990 | Pease et al. | 436/519 |
| 4,931,223 | 6/1990 | Bronstein et al. | 252/700 |
| 4,956,477 | 9/1990 | Bronstein et al. | 549/221 |
| 4,959,182 | 9/1990 | Schaap | 252/700 |
| 4,962,192 | 10/1990 | Schaap | 536/18.1 |
| 4,978,614 | 12/1990 | Bronstein | 435/21 |
| 5,017,473 | 5/1991 | Wagner | 435/7.92 |

FOREIGN PATENT DOCUMENTS

| | | |
|---|---|---|
| 070685 | 1/1983 | European Pat. Off. . |
| 070687 | 1/1983 | European Pat. Off. . |
| 144914 | 6/1985 | European Pat. Off. . |
| 229943 | 7/1987 | European Pat. Off. . |
| 232967 | 8/1987 | European Pat. Off. . |
| 315364 | 11/1987 | European Pat. Off. . |
| 322926 | 7/1989 | European Pat. Off. . |
| 324202 | 7/1989 | European Pat. Off. . |
| 345776 | 12/1989 | European Pat. Off. ................ 435/5 |
| 352713 | 1/1990 | European Pat. Off. . |
| 401001 | 12/1990 | European Pat. Off. . |
| 421788A2 | 4/1991 | European Pat. Off. . |
| WO88/00695 | 1/1988 | PCT Int'l Appl. . |
| WO89/06266 | 7/1989 | PCT Int'l Appl. . |
| WO90/00164 | 1/1990 | PCT Int'l Appl. . |
| WO90/02742 | 3/1990 | PCT Int'l Appl. . |
| WO90/07511 | 7/1990 | PCT Int'l Appl. . |

OTHER PUBLICATIONS

Cardullo et al. Proc. Natl. Acad. Sci. USA. vol. 85 pp. 8790–8794. Dec. 1988.

Hirschfeld, Applied Optics, vol. 15, No. 12:3135–3139 (1976).

Heller, et al., from Rapid Detection and Identification of Infectious Agents, Academic Press, Inc. (1985), pp. 245–257.

Hara, et al., Bull. Chem. Soc. Jpn, vol. 57: pp. 3009–3010 (1984).

Kuschnir, et al., Chemical Communications, vol. 193, (1969).

Cardullo, et al., Proc. Natl. Acad. Sci. U.S.A., vol. 85: pp. 8790–8794 (1988).

Morrison et al., Analytical Biochemistry, vol. 183: pp. 231–244 (1989).

Zomer, et al., Analytica Chemica Acta, vol. 227: pp. 11–19 (1989).

Morrison, Analytical Biochemistry, vol. 174, pp. 101–120 (1988).

O'Connell, et al., Clin. Chem., vol. 31/9, pp. 1424–1426 (1985).

Yemul, et al., Proc. Natl. Acad. Sci. USA, vol. 84: pp. 246–250 (1987).

Mew, et al., Journal of Immunology, vol. 130/3: pp. 1473–1477 (1983).

Oser and Valet, Angew Chem. Int. Ed. Engl., vol. 29:1167–1169 (1990).

*Primary Examiner*—Robert A. Wax
*Assistant Examiner*—David Schmickel
*Attorney, Agent, or Firm*—Theodore J. Leitereg

[57] ABSTRACT

Methods are disclosed for determining an analyte in a medium suspected of containing the analyte. One method comprises providing (1) a medium suspected of containing the analyte, (2) a label reagent comprising a first specific binding pair (sbp) member associated with a photochemically activatable chemiluminescent compound wherein the first sbp member is capable of binding to the analyte or to a second sbp member to form a complex related to the presence of the analyte. The method further comprises photochemically activating the chemiluminescent compound. The amount of luminescence generated by the chemiluminescent compound is detected. The amount thereof is related to the amount of analyte in the medium. Compositions and kits are also disclosed.

86 Claims, No Drawings

ASSAY METHOD UTILIZING PHOTOACTIVATED CHEMILUMINESCENT LABEL

BACKGROUND OF THE INVENTION

1. Field of the Invention

This invention relates to methods, compositions and kits for determining an analyte in a sample.

The clinical diagnostic field has seen a broad expansion in recent years, both as to the variety of materials (analytes) that may be readily and accurately determined, as well as the methods for the determination. Convenient, reliable and non-hazardous means for detecting the presence of low concentrations of materials in liquids is desired. In clinical chemistry these materials may be present in body fluids in concentrations below $10^{-12}$ molar. The difficulty of detecting low concentrations of these materials is enhanced by the relatively small sample sizes that can be utilized.

In developing an assay there are many considerations. One consideration is the signal response to changes in the concentration of analyte. A second consideration is the ease with which the protocol for the assay may be carried out. A third consideration is the variation in interference from sample to sample. Ease of preparation and purification of the reagents, availability of equipment, ease of automation and interaction with material of interest are some of the additional considerations in developing a useful assay.

One broad category of techniques involves the use of a receptor which can specifically bind to a particular spacial and polar organization of a labeled ligand as a function of the presence of the analyte. The observed effect of binding by the receptor will depend upon the label. In some instances the binding of the receptor merely provides for a differentiation in molecular weight between bound and unbound labeled ligand. In other instances the binding of the receptor will facilitate separation of bound labeled ligand from free labeled ligand or it may affect the nature of the signal obtained from the label so that the signal varies with the amount of receptor bound to labeled ligand. A further variation is that the receptor is labeled and the ligand unlabeled. Alternatively, both the receptor and ligand are labeled or different receptors are labeled with different labels where the labels interact when in close proximity and the amount of ligand present affects the degree to which the labels of the receptor may interact.

There is a continuing need for new and accurate techniques that can be adapted for a wide spectrum of different ligands or be used in specific cases where other methods may not be readily adaptable.

Homogeneous immunoassays have previously been described for small molecules. These assays include SYVA's FRAT ® assay, EMIT ® assay, enzyme channeling immunoassay, and fluorescence energy transfer immunoassay (FETI); enzyme inhibitor immunoassays (Hoffman LaRoche and Abbott Laboratories): fluorescence polarization immunoassay (Dandlicker), among others. All of these methods have limited sensitivity, and only a few including FETI and enzyme channeling, are suitable for large multiepitopic analytes.

Luminescent compounds, such as fluorescent compounds and chemiluminescent compounds, find wide application in the assay field because of their ability to emit light. For this reason, luminescers have been utilized as labels in assays such as nucleic acid assays and immunoassays. For example, a member of a specific binding pair is conjugated to a luminescer and various protocols are employed. The luminescer conjugate can be partitioned between a solid phase and a liquid phase in relation to the amount of analyte in a sample suspected of containing the analyte. By measuring the luminescence of either of the phases, one can relate the level of luminescence observed to a concentration of the analyte in the sample.

Particles, such as liposomes and erythrocyte ghosts, have been utilized as carriers of encapsulated water soluble materials. For example, liposomes have been employed to encapsulate biologically active material for a variety of uses, such as drug delivery systems wherein a medicament is entrapped during liposome preparation and then administered to the patient to be treated.

Particles, such as latex beads and liposomes, have also been utilized in assays. For example, in homogeneous assays an enzyme may be entrapped in the aqueous phase of a liposome labelled with an antibody or antigen. The liposomes are caused to release the enzyme in the presence of a sample and complement. Antibody or antigen-labeled liposomes, having water soluble fluorescent or non-fluorescent dyes encapsulated within an aqueous phase vesicle or lipid soluble dyes dissolved in the lipid bilayer of a lipid, have also been utilized to assay for analytes capable of entering into an immunochemical reaction with the surface bound antibody or antigen. Detergents have been used to release the dyes from the aqueous phase of the liposomes.

Chemiluminescent labels offer exceptional sensitivity in ligand binding assays, but one or more chemical activation steps are usually needed. Fluorescent labels do not have this deficiency but are less sensitive.

Chemiluminescent labels have been described for immunoassays and nucleic acid assays where a group, which is covalently bound to a binding partner, on chemical activation emits light. A nucleic and assay kit utilizing an acridinium ester is sold by Genprobe (Pace2 system ®, San Diego, Calif.) and MagicLite ® immunoassay kits using this type of label are sold by CIBA-GEIGY (Basel, Switzerland). Energy transfer from a labeled nucleic acid probe to a fluorescent acceptor bound to a second probe has been described by Heller, et al., I and II, infra, for a sandwich nucleic acid assay. Maggio I, infra, discusses a similar procedure for immunoassays. Transfer of energy from a luminescer covalently bound to a polynucleotide to an intercalated fluorophore was mentioned by Heller, et al., IV, infra. Transfer from an intercalated dye to a fluorescer on a polynucleotide was described recently by Cardullo, et al., infra. Further McCapra, infra, has described the use of photosensitizers as labels where the photosensitizer activates oxygen to its singlet state, which in turn reacts with a compound that on heating produces light.

2. Brief Description of the Related Art

European Patent Application No. 0,345,776 (McCapra) discloses specific binding assays that utilize a sensitizer as a label. The sensitizers include any moiety which, when stimulated by excitation with radiation of one or more wavelengths or other chemical or physical stimulus (e.g., electron transfer, electrolysis, electroluminescence or energy transfer) will achieve an excited state which (a) upon interaction with molecular oxygen will produce singlet molecular oxygen, or (b) upon interaction with a leuco dye will assume a reduced form that can be returned to its original unexcited state by interaction with molecular oxygen resulting in the production of hydrogen peroxide. Either interaction with the excited sensitizer will, with the addition of reagents, produce a detectible signal.

European Patent Application No. 0,070,685 (Heller, et al. I) describes a homogeneous nucleic acid hybridization diagnostic by non-radiative energy transfer.

A light-emitting polynucleotide hybridization diagnostic method is described in European Patent Application No. 0,070,687 (Heller, et al. II).

European Patent Application No. 0,232,967 (Morrison I) discusses methods and compositions for performing assays for target polynucleotide strands. The methods include contacting a sample with a reagent that includes a first and a second polynucleotide probe. The first and second probes are capable of assuming a first position wherein the probes are bound to each other and a second position wherein the probes are bound to a target. The probes include label moieties capable of interacting to produce a signal indicative of the probes being in one of the two positioned.

European Patent Application No. 0,315,364 describes an immunochemical assay to determine the presence or concentration of antigen or antibodies in a fluid. The assay comprises (a) forming a ternary complex of a first labeled antibody or antigen, a second labeled antibody or antigen, and the antigen or antibody to be determined, and (b) detecting a signal produced in the presence of at least one substrate, by an interaction between the first label and the second label, enhanced by their proximity to each other bound to the antigenic substance.

European Patent Application No. 0,229,943 (Heller, et al. III) describes fluorescent Stokes shift probes for a polynucleotide hybridization assays.

U.S. Pat. No. 4,226,993 (Buckler, et al.) describes immuno-functionalized phthalhydrazides, which are useful as intermediates in the synthesis of chemiluminescent phthalhydrazide-labeled conjugates. The conjugates are useful as reagents in specific binding assays for determining ligands or their specific binding partners in liquid media.

U.S. Pat. Nos. 4,380,580 and 4,383,031 (Boguslaski, et al. I and Boguslaski, et al. II) respectively describe heterogeneous and homogeneous chemiluminescent specific binding assays.

U.S. Pat. No. 4,220,450 (Maggio I) discusses chemically induced fluorescence immunoassays.

U.S. Pat. No. 4,652,533 (Jolley) describes a method of solid phase immunoassay incorporating a luminescent label.

U.S. Pat. No. 4,277,437 (Maggio II) discloses kits for carrying out chemically induced fluorescence immunoassays.

Heller, et al. (IV), describe chemiluminescent and fluorescent probes for DNA hybridization systems in "Rapid Detection and Identification of Infectious Agents" (1985) Academic Press, Inc., pages 245-257.

Hara, et al., describe an immunoassay using a metal-complex compound as a chemiluminescent catalyst in *Bull. Chem. Soc. Jpn.* (1984) 57:3009-3010.

Kuschnir, et al., describe photosensitized chemiluminescence of luminol in 6-aminophthalazine-1,4-(2H3H)-dione in *Chemical Communications* (1969) 193.

The detection of nucleic acid hybridization by nonradiative fluorescence residence energy transfer is described by Cardullo, et al., in *Proc. Natl. Acad. Sci. U.S.A.* (1988) 85:8790-8794.

Morrison, et al. describe a solution-phased detection of polynucleotides using interactive fluorescent labels and competitive hybridization in *Analytical Biochemistry* (1989) 183:231-244.

Zomer, et al. describe chemiluminogenic labels in *Analytica Chemica Acta* (1989) 227:11-19.

Morrison II discusses time-resolved detection of energy transfer: theory and application to immunoassays in *Analytical Biochemistry* (1988) 174:101-120.

U.S. Pat. No. 4,299,916 (Litman, et al. I) describes preferential signal production on a surface in immunoassays.

U.S. Pat. No. 4,233,402 (Maggio, et al.) describes reagents and methods employing channeling.

U.S. Pat. No. 4,261,968 (Ullman, et al. I) describes fluorescence quenching with immunological pairs in immunoassays.

U.S. Pat. No. 4,318,707 (Litman, et al. II) discusses a macromolecular fluorescent quencher particle in specific receptor assays.

U.S. Pat. No. 4,650,770 (Liu, et al.) discusses energy absorbing particle quenching in light-emitting competitive protein binding assays.

U.S. Pat. No. 4,654,300 (Zuk, et al.) describes a fluorescent microbead quenching assay.

U.S. Pat. No. 4,174,384 (Ullman, et al. II) describes fluorescence quenching with immunological pairs in immunoassays.

U.S. Pat. No. 4,193,983 (Ullman, et al. III) discloses labeled liposome particle compositions and immunoassays therewith.

U.S. Pat. Nos. 4,199,559 and 3,996,345 (Ullman, et al. IV and V) describes fluroescence quenching with immunological pairs in immunoassays.

O'Connell, et al., *Clin. Chem.*, (1985) 31(9), 1424-1426 discloses a colorimetric immunoassay for digoxin utilizing large, unilamellar phospholipid vesicles having dye entrapped in the aqueous phase of the liposome.

U.S. Pat. No. 3,850,578 (McConnell); U.S. Pat. No. 4,483,921 (Yaverbaum); and U.S. Pat. No. 4,483,929 (Szoka) disclose immunoreactive liposome reagents in which antigen or antibody is bound to the surface of lipid vesicles.

U.S. Pat. No. 4,529,561 (Hunt, et al.); U.S. Pat. No. 4,522,803 (Lenk, et al.); and U.S. Pat. No. 4,485,054 (Mezei, et al.) disclose a variety of methods for preparing lipid vesicles.

U.S. Pat. No. 4,311,712 (Evans, et al.) discloses a process for preparing a freeze dried liposome mixture.

U.S. Pat. No. 4,588,578 (Fountain, et al.) discloses a method for the preparation of monophasic lipid vesicles and the use of such vesicles for drug delivery systems.

U.S. Pat. No. 4,576,912 discloses a method of enhancing the fluorescent level of an immunoassay using certain long-chain carriers tagged with a plurality of fluorophores.

U.S. Pat. No. 4,891,324 describes a particle with luminescer for assays.

Selective killing of T lymphocytes by phototoxic liposomes is described by Yemu, et al. (1987) *Proc. Natl. Acad. Sci. U.S.A.*, 84: 246-250.

Mew, et al. in *J. of Immunology*, 130(3): 1473-1477 (1983) discloses photoimmunotherapy: treatment of animal tumors with tumor-specific monoclonal antibody-hematoporphyrin conjugates.

Optical microscopic observation of single small molecules is discussed by Hirschfeld (1976) *Applied Optics,* 15(12): 3135–3139.

European Patent Application 0 322 926 (McCapra, et al.) describes assays utilizing improved chemiluminescent esters, thioesters, and amides.

European Patent Application 0 352 713 (Schaap) describes a method and compositions providing enhanced chemiluminescence from 1,2-dioxetanes.

U.S. Pat. No. 4,978,614 (Bronstein) discloses a method of detecting a substance using enzymatically-induced decomposition of dioxetanes.

Bronstein, et al. (U.S. Pat. No. 4,956,477), discuss the synthesis of 1,2-dioxetanes.

Schaap, et al., describe enhanced luminescence from 1,2-dioxetanes through energy transfer to tethered fluorescers in WO 90/07511.

U.S. Pat. No. 4,959,182 (Schaap) discloses a method and compositions providing enhanced chemiluminescence from 1,2-dioxetanes.

U.S. Pat. No. 4,962,192 (Schaap) and U.S. Pat. No. 4,857,652 (Schaap) describe chemiluminescent 1,2-dioxetane compounds.

Bronstein, et al., describe a method using chemiluminescent 1,2-dioxetanes in U.S. Pat. No. 4,931,223.

The purification of stable water-soluble dioxetanes is disclosed in WO 90/02742 (Edwards, et al.).

Novel Chemiluminescent fused polycyclic ring-containing 1,2-dioxetanes and assays in which they are used are described in WO 90/00164 (Edwards, et al.)

WO 89/06226 (Edwards, et al.) discusses the synthesis of 1,2-dioxetanes and intermediates therefor.

Neckers, et al., describe polymer-bound photosensitizing catalysts in U.S. Pat. No. 4,315,998.

A method of detecting a substance using enzymatically-induced decomposition of dioxetanes is discussed in WO 88/00695 (Bronstein, et al.).

European Patent Application 0 324 202 (Zomer, et al.) discloses acridinium compounds as chemiluminogenic labels.

European Patent Application 0 144 914 (Alberella, et al.) describes a hybridization assay employing labeled pairs of hybrid binding reagents.

European Patent Application 0 401 001 (Urdea, et al.) describes chemiluminescent double-triggered 1,2-dioxetanes.

SUMMARY OF THE INVENTION

The present invention is directed to methods for determining an analyte. One embodiment of a method in accordance with the present invention comprises providing (1) a medium suspected of containing the analyte, (2) a label reagent comprising a first specific binding pair (sbp) member associated with a photochemically activatable chemiluminescent compound wherein the first sbp member is capable of binding to the analyte or a second sbp member to form a complex related to the presence of the analyte, photochemically activating the chemiluminescent compound, and detecting the amount of luminescence generated by the chemiluminescent compound, the amount thereof being related to the amount of analyte in the medium.

In another embodiment the method of the present invention for determining an analyte comprises as a first step combining in an assay medium (1) a medium suspected of containing an analyte, and (2) a label reagent comprising a member of a specific binding pair (sbp member) bound to a photochemically activatable chemiluminescent compound under conditions wherein an sbp member complex involving the label reagent is formed in relation to the presence of analyte in the medium. The assay medium is irradiated with light to activate the photochemically activatable chemiluminescent compound. The assay medium is examined for a light emission. The presence or intensity of such signal light emission is related to the amount of analyte in said medium. An energy acceptor is included in the medium where the energy from the chemiluminescent compound is capable of activating the energy acceptor.

Another embodiment is a method for determining an analyte. The method comprises combining in an aqueous medium either simultaneously or wholly or partially sequentially (1) a medium suspected of containing an analyte, (2) a label reagent comprising a first member of a specific binding pair (sbp member) bound to a compound capable of chemiluminescence upon reaction with light or singlet oxygen, and (3) an insolubilized reagent comprising an energy acceptor bound to, or capable of becoming bound to, a second sbp member. Conditions are chosen wherein an sbp member complex involving the label reagent is formed in relation to the presence of analyte in the medium and energy from the chemiluminescent compound is capable of activating the energy acceptor. The compound is activated with light or singlet oxygen. The assay medium is examined for luminescence, the presence or intensity thereof being related to the amount of analyte in the medium.

Another embodiment of the invention is a method for determining an analyte where the method comprises: (a) combining in an assay medium either simultaneously or wholly or partially sequentially (1) a medium suspected of containing an analyte, (2) a label reagent comprising a first member of a specific binding pair (sbp member) bound to a compound capable of chemiluminescence upon reaction with singlet oxygen, (3) a singlet oxygen generator, and (4) a reagent comprising an energy acceptor bound to, or capable of becoming bound to, a second sbp member, under conditions wherein an sbp member complex involving the label reagent is formed in relation to the presence of analyte in the medium and energy from the chemiluminescent compound is capable of activating the energy acceptor, (b) activating the singlet oxygen generator, and (c) examining the assay medium for a signal, the presence or intensity thereof being related to the amount of analyte in the medium.

Another embodiment of the present invention is a method for determining a polynucleotide analyte, where the method comprising (a) combining in an assay medium, (1) a sample suspected of containing a polynucleotide analyte and (2) a label reagent comprising a photochemically activatable chemiluminescent compound bound to a polynucleotide, at least a portion of which is capable of hybridizing with said polynucleotide analyte, under conditions wherein the label reagent hybridizes with the polynucleotide analyte if present, (b) irradiating the assay medium to activate the photochemically activatable chemiluminescent compound, and (c) measuring the luminescence of the medium. The amount of luminescence is related to the amount of analyte in the sample.

Another embodiment of the invention is a composition comprising a photochemically activatable chemiluminescent compound bound to an sbp member.

Another embodiment of the invention is a kit comprising the above composition.

DESCRIPTION OF THE SPECIFIC EMBODIMENTS

In the present invention a group that can be photochemically activated to a luminescent product is used as a label. The group is associated with a member of a specific binding pair and this reagent is utilized as a labeled reagent in assays for detection of an analyte. Photochemical activation can be achieved by irradiating the group with light or by reaction singlet with the group. Preferably, a sensitizer is used to assist photoactivation where activation is by singlet oxygen. Usually the sensitizer absorbs light and the thus formed excited sensitizer activates oxygen and the singlet oxygen reacts with the label to give a metastable luminescent intermediate. The group used as a label may include any chemiluminescent compound that undergoes photoactivation with or without sensitization and preferably is a group that is activated by reaction with singlet oxygen. The labels of the present invention can be used in both homogeneous and heterogeneous assay protocols to determine an analyte. Desirably, no addition of chemical reagents is required to activate the chemiluminescent compound with or without a sensitizer and energy acceptor. In a homogeneous protocol all the reagents are combined and the medium is irradiated to activate the chemiluminescent compound.

In the assay protocol the components are combined and the light produced as a function of irradiation will be a function of analyte concentration. Advantageously, the methods of the present invention can be carried out without heating the medium to produce light. Consequently, the assay of the present invention can be conducted at a constant temperature.

Before proceeding further with a description of the specific embodiments of the present invention, a number of terms will be defined and described in detail.

Analyte—the compound or composition to be detected. The analyte can be comprised of a member of a specific binding pair (sbp) and may be a ligand, which is monovalent (monoepitopic) or polyvalent (polyepitopic), usually antigenic or haptenic, and is a single compound or plurality of compounds which share at least one common epitopic or determinant site. The analyte can be a part of a cell such as bacteria or a cell bearing a blood group antigen such as A, B, D, etc., or an HLA antigen or a microorganism, e.g., bacterium, fungus, protozoan, or virus.

The polyvalent ligand analytes will normally be poly(amino acids), i.e., polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes to which the subject invention can be applied will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc.

The following are classes of proteins related by structure:
protamines
histones
albumins
globulins
scleroproteins
phosphoproteins
mucoproteins
chromoproteins
lipoproteins
nucleoproteins
glycoproteins
T-cell receptors
proteoglycans
HLA
unclassified proteins, e.g., somatotropin, prolactin, insulin, pepsin A number of proteins found in the human plasma are important clinically and include:
Prealbumin
Albumin
$\alpha_1$-Lipoprotein
$\alpha_1$-Antitrypsin
$\alpha_1$-Glycoprotein
Transcortin
4.6S-Postalbumin
Tryptophan-poor
   $\alpha_1$-glycoprotein
$\alpha_1$X-Glycoprotein
Thyroxin-binding globulin
Inter-$\alpha$-trypsin-inhibitor
Gc-globulin
   (Gc 1-1)
   (Gc 2-1)
   (Gc 2-2)
Haptoglobin
   (Hp 1-1)
   (Hp 2-1)
   (Hp 2-2)
Ceruloplasmin
Cholinesterase
$\alpha_2$-Lipoprotein(s)
Myoglobin
C-Reactive Protein
$\alpha_2$-Macroglobulin
$\alpha_2$-HS-glycoprotein
Zn-$\alpha_2$-glycoprotein
$\alpha_2$-Neuramino-glycoprotein
Erythropoietin
$\beta$-lipoprotein
Transferrin
Hemopexin
Fibrinogen
Plasminogen
$\beta_2$-glycoprotein I
$\beta_2$-glycoprotein II
Immunoglobulin G
   (IgG) or $\gamma$G-globulin
Mol. formula:
   $\gamma 2k2$ or $\gamma 2\lambda 2$
Immunoglobulin A (IgA)
   or $\gamma$A-globulin
Mol. formula:

$(\alpha_2 \kappa_2)^n$ or $(\alpha_2 \kappa_2)^n$
Immunoglobulin M
(IgM) or γM-globulin
Mol. formula:
$(\mu_2 \kappa_2)^5$ or $(\mu_2 \lambda_2)^5$
Immunoglobulin D (IgD)
or γD-Globulin (γD)
Mol. formula:
$(\delta_2 \kappa_2)$ or $\delta_2 \lambda_2$)
Immunoglobulin E (IgE)
or γE-Globulin (γE)
Mol. formula:
$(\epsilon_2 \kappa_2)$ or $(\epsilon_2 \lambda_2)$
Free κ and λ light chains
Complement factors:
C'1
  C'1q
  C'1r
  C'1s
C'2
C'3
  $\beta_1$A
  $\alpha_2$D
C'4
C'5
C'6
C'7
C'8
C'9
Important blood clotting factors include:

| International designation | Name |
|---|---|
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

Important protein hormones include:

Peptide and Protein Hormones
Parathyroid hormone
(parathromone)
Thyrocalcitonin
Insulin
Glucagon
Relaxin
Erythropoietin
Melanotropin
(melancyte-stimulating)
hormone; intermedin)
Somatotropin
(growth hormone)
Corticotropin
(adrenocorticotropic hormone)
Thyrotropin
Follicle-stimulating hormone
Luteinizing hormone
(interstitial cell-stimulating hormone)
Luteomammotropic hormone
(luteotropin, prolactin
Gonadotropin
(chorionic gonadotropin)

Tissue Hormones
Secretin
Gastrin
Angiotensin I and II
Bradykinin
Human placental lactogen Cytokines
IL I
IL II
IL VI
EGF
TNF
NGF Cancer Antigens
PSA
CEA
α-fetoprotein
Acid phosphatase
CA19.9
CA125

Tissue Specific Antigens
alkaline phosphatase
myoglobin
CPK-MB
calcitonin
Myelin basic protein Peptide Hormones from the Neurohypophysis
Oxytocin
Vasopressin
Releasing factors (RF)
CRF, LRF, TRF, Somatotropin-RF,
GRF, FSH-RF, PIF, MIF Other polymeric materials of interest are mucopolysaccharides and polysaccharides. Illustrative microorganisms include:

| | |
|---|---|
| Corynebacteria | |
| *Corynebacterium diphtheria* | |
| Pneumococci | |
| *Diplococcus pneumoniae* | |
| Streptococci | |
| *Streptococcus pyogenes* | |
| *Streptococcus salivarus* | |
| Staphylococci | |
| *Staphylococcus aureus* | |
| *Staphylococcus albus* | |
| Neisseria | |
| *Neisseria meningitidis* | |
| *Neisseria gonorrhea* | |
| Enterobacteriaciae | |
| *Escherichia coli* | |
| *Aerobacter aerogenes* | The coliform |
| *Klebsiella pneumoniae* | bacteria |

-continued

| | |
|---|---|
| *Salmonella typhosa* | |
| *Salmonella choleraesuis* | The Salmonellae |
| *Salmonella typhimurium* | |
| *Shigella dysenteria* | |
| *Shigella schmitzii* | |
| *Shigella arabinotarda* | |
| | The Shigellae |
| *Shigella flexneri* | |
| *Shigella boydii* | |
| *Shigella sonnei* | |
| Other enteric bacilli | |
| *Proteus vulgaris* | |
| *Proteus mirabilis* | Proteus species |
| *Proteus morgani* | |
| *Pseudomonas aeruginosa* | |
| *Alcaligenes faecalis* | |
| *Vibrio cholerae* | |
| Hemophilus-Bordetella group | *Rhizopus oryzae* |
| *Hemophilus influenza, H. ducryi* | *Rhizopus arrhizua* |
| | Phycomycetes |
| *Hemophilus hemophilus* | *Rhizopus nigricans* |
| *Hemophilus aegypticus* | *Sporotrichum schenkii* |
| *Hemophilus parainfluenza* | *Flonsecaea pedrosoi* |
| *Bordetella pertussis* | *Fonsecacea compact* |
| Pasteurellae | *Fonsecacea dermatidis* |
| *Pasteurella pestis* | *Cladosporium carrionii* |
| *Pasteurella tulareusis* | *Phialophora verrucosa* |
| Brucellae | *Aspergillus nidulans* |
| *Brucella melitensis* | *Madurella mycetomi* |
| *Brucella abortus* | *Madurella grisea* |
| *Brucella suis* | *Allescheria boydii* |
| Aerobic Spore-forming Bacilli | *Phialophora jeanselmei* |
| *Bacillus anthracis* | *Microsporum gypseum* |
| *Bacillus subtilis* | *Trichophyton mentagrophytes* |
| *Bacillus megaterium* | *Keratinomyces ajelloi* |
| *Bacillus cereus* | *Microsporum canis* |
| Anaerobic Spore-forming Bacilli | *Trichophyton rubrum* |
| *Clostridium botulinum* | *Microsporum adouini* |
| *Clostridium tetani* | Viruses |
| *Clostridium perfringens* | Adenoviruses |
| *Clostridium novyi* | Herpes Viruses |
| *Clostridium septicum* | Herpes simplex |
| *Clostridium histolyticum* | Varicella (Chicken pox) |
| *Clostridium tertium* | Herpes Zoster (Shingles) |
| *Clostridium bifermentans* | Virus B |
| *Clostridium sporogenes* | Cytomegalovirus |
| Mycobacteria | Pox Viruses |
| *Mycobacterium tuberculosis hominis* | Variola (smallpox) |
| *Mycobacterium bovis* | Vaccinia |
| *Mycobacterium avium* | *Poxvirus bovis* |
| *Mycobacterium leprae* | Paravaccinia |
| *Mycobacterium paratuberculosis* | *Molluscum contagiosum* |
| Actinomycetes (fungus-like bacteria) | Picornaviruses |
| Actinomyces Isaeli | Poliovirus |
| *Actinomyces bovis* | Coxsackievirus |
| *Actinomyces naeslundii* | Echoviruses |
| *Nocardia asteroides* | Rhinoviruses |
| *Nocardia brasiliensis* | Myxoviruses |
| The Spirochetes | Influenza(A, B, and C) |
| *Treponema pallidum*    *Spirillum minus* | Parainfluenza (1–4) |
| *Treponema pertenue*    *Streptobacillus monoiliformis* | Mumps Virus |
| | Newcastle Disease Virus |
| *Treponema carateum* | Measles Virus |
| *Borrelia recurrentis* | Rinderpest Virus |
| *Leptospira icterohemorrhagiae* | Canine Distemper Virus |
| *Leptospira canicola* | Respiratory Syncytial Virus |
| Trypanasomes | Rubella Virus |
| Mycoplasmas | Arboviruses |
| *Mycoplasma pneumoniae* | |
| Other pathogens | Eastern Equine Encephalitis Virus |
| *Listeria monocytogenes* | Western Equine Encephalitis Virus |
| *Erysipelothrix rhusiopathiae* | Sindbis Virus |
| *Streptobacillus moniliformis* | Chikugunya Virus |
| *Donvania granulomatis* | Semliki Forest Virus |
| *Bartonella bacilliformis* | Mayora Virus |

| -continued | |
|---|---|
| Rickettsiae (bacteria-like parasites) | St. Louis Encephalitis Virus |
| Rickettsia prowazekii | California Encephalitis Virus |
| Rickettsia mooseri | Colorado Tick Fever Virus |
| Rickettsia rickettsii | Yellow Fever Virus |
| Rickettsia conori | Dengue Virus |
| Rickettsia australis | Reoviruses |
| Rickettsia sibiricus | Reovirus Types 1–3 |
| | Retroviruses |
| Rickettsia akari | Human Immunodeficiency |
| Rickettsia tsutsugamushi | Viruses I and II (HIV) |
| | Human T-cell Lymphotrophic Virus I & II (HTLV) |
| Rickettsia burnetti | Hepatitis |
| Rickettsia quintana | Hepatitis A Virus |
| Chlamydia (unclassifiable parasites | Hepatitis B Virus |
| bacterial/viral) | Hepatitis C Virus |
| Chlamydia agents (naming uncertain) | Tumor Viruses |
| Fungi | Rauscher Leukemia Virus |
| Cryptococcus neoformans | Gross Virus |
| Blastomyces dermatidis | Maloney Leukemia Virus |
| Hisoplasma capsulatum | |
| Coccidioides immitis | Human Papilloma Virus |
| Paracoccidioides brasiliensis | |
| Candida albicans | |
| Aspergillus fumigatus | |
| Mucor corymbifer (Absidia corymbifera) | |

The monoepitopic ligand analytes will generally be from about 100 to 2,000 molecular weight, more usually from 125 to 1,000 molecular weight. The analytes include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites.

The next group of drugs includes steroids, which includes the estrogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbituates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines; catecholamines, which includes ephedrine, L-dopa, epinephrine; narceine; papaverine; and metabolites of the above.

The next group of drugs is benzheterocyclics which include oxazepam, chlorpromazine, tegretol, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs is the hormones such as thyroxine, cortisol, triiodothyronine, testosterone, estradiol, estrone, progestrone, polypeptides such as angiotensin, LHRH, and immunosuppresants such as cyclosporin, FK506, mycophenolic acid, and so forth.

The next group of drugs includes the vitamins such as A, B, e.g. B12, C, D, E and K, folic acid, thiamine.

The next group of drugs is prostaglandins, which differ by the degree and sites of hydroxylation and unsaturation.

The next group of drugs is the tricyclic antidepressants, which include imipramine, dismethylimipramine, amitriptyline, nortriptyline, protriptyline, trimipramine, chlomipramine, doxepine, and desmethyldoxepin, The next group of drugs are the anti-neoplastics, which include methotrexate.

The next group of drugs is antibiotics, which include penicillin, chloromycetin, actinomycetin, tetracycline, terramycin, the metabolites and derivatives.

The next group of drugs is the nucleosides and nucleotides, which include ATP, AND, FMN, adenosine, guanosine, thymidine, and cytidine with their appropriate sugar and phosphate substituents.

The next group of drugs is miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

The term analyte further includes polynucleotide analytes such as those polynucleotides defined below. These include m-RNA, r-RNA, t-RNA, DNA, DNA-RNA duplexes, etc. The term analyte also includes receptors that are polynucleotide binding agents, such as, for example, restriction enzymes, activators, repressors, nucleases, polymerases, histones, repair enzymes, chemotherapeutic agents, and the like.

The analyte may be a molecule found directly in a sample such as a body fluid from a host. The sample can be examined directly or may be pretreated to render the analyte more readily detectable. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The body fluid can be, for example, urine, blood, plasma, serum, saliva, semen, stool, sputum, cerebral spinal fluid, tears, mucus, and the like.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the invention and the definition of sbp member.

Polynucleotide—a compound or composition which is a polymeric nucleotide having in the natural state about 50 to 500,000 or more nucleotides and having in the isolated state about 15 to 50,000 or more nucleotides, usually about 15 to 20,000 nucleotides, more frequently 15 to 10,000 nucleotides. The polynucleotide includes nucleic acids from any source in purified or unpurified form, naturally occurring or synthetically produced, including DNA (dsDNA and ssDNA) and RNA, usually DNA, and may be t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like.

Ligand—any organic compound for which a receptor naturally exists or can be prepared.

Ligand analog—a modified ligand, an organic radical or analyte analog, usually of a molecular weight greater than 100, which can compete with the analogous ligand for a receptor, the modification providing means to join a ligand analog to another molecule. The ligand analog will usually differ from the ligand by more than replacement of a hydrogen with a bond which links the ligand analog to a hub or label, but need not. The ligand analog can bind to the receptor in a manner similar to the ligand. The analog could be, for example, an antibody directed against the idiotype of an antibody to the ligand.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component Clq, and the like.

Specific binding—the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme - substrate interactions, polynucleotide interactions, and so forth.

Non-specific binding—non-covalent binding between molecules that is relatively independent of specific surface structures. Non-specific binding may result from several factors including hydrophobic interactions between molecules.

Antibody—an immunoglobulin which specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab' and the like In addition, aggregates, polymers, and conjugates of immunoglobulins or their fragments can be used where appropriate so long as binding affinity for a particular molecule is maintained.

Alkyl—a monovalent branched or unbranched radical derived from an aliphatic hydrocarbon by removal of one H atom; includes both lower alkyl and upper alkyl.

Lower alkyl—alkyl containing from 1 to 5 carbon atoms such as, e.g., methyl, ethyl, propyl, butyl, isopropyl, isobutyl, pentyl, isopentyl, etc.

Upper alkyl—alkyl containing more than 6 carbon atoms, usually 6 to 20 carbon atoms, such as, e.g., hexyl, heptyl, octyl, etc.

Alkylidene—a divalent organic radical derived from an aliphatic hydrocarbon, such as, for example, ethylidene, in which 2 hydrogen atoms are taken from the same carbon atom.

Aryl—an organic radical derived from an aromatic hydrocarbon by the removal of one atom and containing one or more aromatic rings, usually one to four aromatic rings, such as, e.g., phenyl (from benzene), naphthyl (from naphthalene), etc.

Aralkyl—an organic radical having an alkyl group to which is attached an aryl group, e.g., benzyl, phenethyl, 3-phenylpropyl, 1-naphthylethyl, etc.

Alkoxy—an alkyl radical attached to the remainder of a molecule by an oxygen atom, e.g., methoxy, ethoxy, etc.

Aryloxy—an aryl radical attached to the remainder of a molecule by an oxygen atom, e.g., phenoxy, naphthoxy, etc.

Aralkoxy—an aralkyl radical attached to the remainder of a molecule by an oxygen atom, e.g., benzoxy, 1-naphthylethoxy, etc.

Substituted—means that a hydrogen atom of a molecule has been replaced by another atom, which may be a single atom such as a halogen, etc., or part of a group of atoms forming a functionality such as a substituent having from 1 to 50 atoms (other than the requisite hydrogen atoms necessary to satisfy the valencies of such atoms), which atoms are independently selected from the group consisting of carbon, oxygen, nitrogen, sulfur and phosphorus, and which may or may not be bound to one or more metal atoms.

Alkylthio—an alkyl radical attached to the remainder of a molecule by a sulfur atom, e.g., methylthio, ethylthio, etc.

Arylthio—an aryl radical attached to the remainder of a molecule by a sulfur atom, e.g., phenylthio, naphthylthio, etc.

Electron-donating group—a substituent which when bound to a molecule is capable of polarizing the molecule such that the electron-donating group becomes electron poor and positively charged relative to another portion of the molecule, i.e., has reduced electron density. Such groups may be, by way of illustration and not limitation, amines, ethers, thioethers, phosphines, hydroxy, oxyanions, mercaptans and their anions, sulfides, etc.

A substituent having from 1 to 50 atoms (other than the requisite hydrogen atoms necessary to satisfy the valencies of such atoms), which atoms are independently selected from the group consisting of carbon, oxygen, nitrogen, sulfur and phosphorus—an organic radical; the organic radical has 1 to 50 atoms other than the requisite number of hydrogen atoms necessary to satisfy the valencies of the atoms in the radical. Generally, the predominant atom is carbon (C) but may also be oxygen (O), nitrogen (N), sulfur (S), phosphorus (P), wherein the O, N, S, or P, if present, are bound to carbon or one or more of each other or to hydrogen or a metal atom to form various functional groups, such as, for example, carboxylic acids, alcohols, thiols, carboxamides, carbamates, carboxylic acid esters, sulfonic acids, sulfonic acid esters, phosphoric acids, phosphoric acid esters, ureas, carbamates, phosphoramides, sulfonamides, ethers, sulfides, thioethers, olefins, acetylenes, amines, ketones, aldehydes, nitriles, and the like. Illustrative of such organic radicals or groups, by way of illustration and not limitation, are alkyl, alkylidine, aryl, aralkyl, and alkyl, aryl, and aralkyl substituted with one or more of the aforementioned functionalities.

Linking group-the covalent linkage between molecules. The linking group will vary depending upon the nature of the molecules, i.e., photosensitizer, chemiluminescent compound, sbp member or molecule associated with or part of a particle, being linked. Functional groups that are normally present or are introduced on a photosensitizer or chemiluminescent compound will be employed for linking these materials to an sbp member or a particle such as a lipophilic component of a liposome or oil droplet, latex particle, silicon particle, metal sol, or dye crystallite.

For the most part, carbonyl functionalities will find use, both oxocarbonyl, e.g., aldehyde and non-oxocarbonyl (including nitrogen and sulfur analogs) e.g., carboxy, amidine, amidate, thiocarboxy and thionocarboxy.

Alternative functionalities of oxo include active halogen, diazo, mercapto, olefin, particularly activated olefin, amino, phosphoro and the like. A description of linking groups may be found in U.S. Pat. No. 3,817,837, which disclosure is incorporated herein by reference.

The linking groups may vary from a bond to a chain of from 1 to 100 atoms, usually from about 1 to 70 atoms, preferably 1 to 50 atoms more preferably 1 to 20 atoms, each independently selected from the group normally consisting of carbon, oxygen, sulfur, nitrogen and phosphorous. The number of heteroatoms in the linking groups will normally range from about 0 to 20, usually from about 1 to 15, more preferably 2 to 6. The atoms in the chain may be substituted with atoms other than hydrogen in a manner similar to that described for the substituent having from 1 to 50 atoms. As a general rule, the length of a particular linking group can be selected arbitrarily to provide for convenience of synthesis and the incorporation of any desired group such as an energy acceptor, fluorophor, group for analysis of intersystem crossing such as a heavy atom, and the like. The linking groups may be aliphatic or aromatic, although with diazo groups, aromatic groups will usually be involved.

When heteroatoms are present, oxygen will normally be present as oxo or oxy, bonded to carbon, sulfur, nitrogen or phosphorous, nitrogen will normally be present as nitro, nitroso or amino, normally bonded to carbon, oxygen, sulfur or phosphorous; sulfur would be analogous to oxygen; while phosphorous will be bonded to carbon, sulfur, oxygen or nitrogen, usually as phosphonate and phosphate mono- or diester.

Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters.

For the most part, the photosensitizer and photochemically activatable chemiluminescent compound will have a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or $\alpha, \beta$-unsaturated ester. These functionalities will be linked to amine groups, carboxyl groups, active olefins, alkylating agents, e.g., bromoacetyl. Where an amine and carboxylic acid or its nitrogen derivative or phophoric acid are linked, amides, amidines and phosphoramides will be formed. Where mercaptan and activated olefin are linked, thioethers will be formed. Where a mercaptan and an alkylating agent are linked, thioethers will be formed. Where aldehyde and an amine are linked under reducing conditions, an alkylamine will be formed. Where a carboxylic acid or phosphate acid and an alcohol are linked, esters will be formed.

A group or functionality imparting hydrophilicity or water solubility—is a hydrophilic functionality, which increases wettability of solids with water and the solubility in water of compounds to which it is bound. Such functional group or functionality can be a substituent having 1 to 50 or more atoms and can include a sulfonate, sulfate, phosphate, amidine, phosphonate, carboxylate, hydroxyl particularly polyols, amine, ether, amide, and the like. Illustrative functional groups are carboxyalkyl, sulfonoxyalkyl, $CONHOCH_2COOH$, CO-(glucosamine), sugars, dextran, cyclodextrin, $SO_2NHCH_2COOH$, $SO_3H$, $CONHCH_2CH_2SO_3H$, $PO_3H_2$, $OPO_3H_2$, hydroxyl, carboxyl, ketone, and combinations thereof. Most of the above functionalities can also be utilized as attaching groups, which permit attachment of the photosensitizer or chemiluminescent compound to an sbp member or a support.

A group or functionality imparting lipophilicity or lipid solubility—is a lipophilic functionality, which decreases the wettability of surfaces by water and the solubility in water of compounds to which it is bound. Such functional group or functionality can contain 1 to 50 or more atoms, usually carbon atoms substituted with hydrogen or halogen and can include alkyl, alkylidene, aryl and aralkyl. The lipophilic group or functionality will normally have one to six straight or branched chain aliphatic groups of at least 6 carbon atoms, more usually at least 10 carbon atoms, and preferably at least 12 carbon atoms, usually not more than 30 carbon atoms. The aliphatic group may be bonded to rings of from 5 to 6 members, which may be alicyclic, heterocyclic, or aromatic.

Photosensitizer—a sensitizer for generation of singlet oxygen usually by excitation with light. The photosensitizer can be photoactivatable (e.g., dyes and aromatic compounds) or chemi-activated (e.g., enzymes and metal salts). When excited by light the photosensitizer is usually a compound comprised of covalently bonded atoms, usually with multiple conjugated double or triple bonds. The compound should absorb light in the wavelength range of 200–1100 nm, usually 300–1000 nm, preferably 450–950 nm, with an extinction coefficient at its absorbance maximum greater than 500 $M^{-1}cm^{-1}$, preferably at least 5000 $M^{-1}cm^{-1}$, more preferably at least 50,000 $M^{-1}cm^{-1}$ at the excitation wavelength. The lifetime of an excited state produced following absorption of light in the absence of oxygen will usually be at least 100 nsec, preferably at least 1 msec. In general, the lifetime must be sufficiently long to permit energy transfer to oxygen, which will normally be present at concentrations in the range of $10^{-5}$ to $10^{-3}M$ depending on the medium. The photosensitizer excited state will usually have a different spin quantum number (S) than its ground state and will usually be a triplet (S=1) when, as is usually the case, the ground state is a singlet (S=O). Preferably, the photosensitizer will have a high intersystem crossing yield. That is, photoexcitation of a photosensitizer will produce the long lived state (usually triplet) with an efficiency of at least 10%, desirably at least 40%, preferably greater than 80%. The photosensitizer will usually be at most weakly fluorescent under the assay conditions (quantum yield usually less that 0.5, preferably less that 0.1).

Photosensitizers that are to be excited by light will be relatively photostable and will not react efficiently with singlet oxygen. Several structural features are present in most useful photosensitizers. Most photosensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3–6 of the periodic table, especially iodine or bromine, or they may have extended aromatic structures. Typical photosensitizers include acetone, benzophenone, 9-thioxanthone, eosin, 9,10-dibromoanthracene, methylene blue, metallo-porphyrins, such as hematoporphyrin, phthalocyanines, chlorophylls, rose bengal, buckminsterfullerene, etc., and derivatives of these compounds having substituents of 1 to 50 atoms for rendering such compounds more lipophilic or more hydrophilic and/or as attaching groups for attachment, for example, to an sbp member. Examples of other photosensitizers that may be utilized in the present invention are those that have the above properties and are enumerated in N. J. Turro, "Molecular Photochemistry" page 132 W. A. Benjamin Inc., N.Y. 1965.

The photosensitizers are preferably relatively nonpolar to assure dissolution into a lipophilic member when the photosensitizer is incorporated in an oil droplet, liposome, latex particle, etc.

The photosensitizers useful in this invention are also intended to include other substances and compositions that can produce singlet oxygen with or, less preferably, without activation by an external light source. Thus, for example, molybdate ($MOO_4^=$) salts and chloroperoxidase and myeloperoxidase plus bromide or chloride ion (Kanofsky, *J. Biol. Chem.* (1983) 259 5596) have been shown to catalyze the conversion of hydrogen peroxide to singlet oxygen and water. Either of these compositions can, for example, be included in particles to which is bound an sbp member and used in the assay method wherein hydrogen peroxide is included as an ancillary reagibly, chloroperoxidase is bound to a surface and molybdate is incorporated in the aqueous phase of a liposome. Also included within the scope of the invention as photosensitizers are compounds that are not true sensitizers but which on excitation by heat, light, or chemical activation will release a molecule of singlet oxygen. The best known members of this class of compounds includes the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen.

Support or surface-a surface comprised of a porous or non-porous water insoluble material. The surface can have any one of a number of shapes, such as strip, rod, particle, including bead, and the like. The surface can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to the support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970).

The surface will usually be polyfunctional or be capable of being polyfunctionalized or be capable of binding an oligonucleotide, an sbp member, a photosensitizer, and/or a photochemically activatable chemiluminescent compound through specific or non-specific covalent or non-covalent interactions. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to surfaces is well known and is amply illustrated in the literature. See for example Cautrecasas, *J. Biol. Chem.* 245,3059 (1970). The length of a linking group to the oligonucleotide or sbp member may vary widely, depending upon the nature of the compound being linked, the effect of the distance between the compound being linked and the surface on the specific binding properties and the like.

Particles-particles of at least about 20 nm and not more than about 20 microns, usually at least about 40 nm and less than about 10 microns, preferably from about 0.10 to 2.0 microns diameter, normally having a volume of less than 1 picoliter. The particle may be organic or inorganic, swellable or non-swellable, porous or non-porous, having any density, but preferably of a density approximating water, generally from about 0.7 to about 1.5g/ml, preferably suspendible in water, and composed of material that can be transparent, partially transparent, or opaque. The particles may or may not have a charge, and when they are charged, they are preferably negative. The particles may be solid (e.g., polymer, metal, glass, organic and inorganic such as minerals, salts and diatoms), oil droplets (e.g., hydrocarbon, fluorocarbon, silicon fluid), or vesicles (e.g., synthetic such as phospholipid or natural such as cells and organelles). The particles may be latex particles or other particles comprised of organic or inorganic polymers; lipid bilayers, e.g., liposomes, phospholipid vesicles; oil droplets; silicon particles; metal sols; cells; and dye crystallites.

The organic particles will normally be polymers, either addition or condensation polymers, which are readily dispersible in the assay medium. The organic particles will also be adsorptive or functionalizable as to bind at their surface, either directly or indirectly, an sbp member and to bind at their surface or incorporate within their volume a photosensitizer or a photochemically activatable chemiluminescent compound.

The particles can be derived from naturally occurring materials, naturally occurring materials which are synthetically modified and synthetic materials. Natural or synthetic assemblies such as lipid bilayers, e.g., liposomes and non-phospholipid vesicles, are preferred. Among organic polymers of particular interest are polysaccharides, particularly cross-linked polysaccharides, such as agarose, which is available as Sepharose, dextran, available as Sephadex and Sephacryl, cellulose, starch, and the like; addition polymers, such as polystyrene, polyacrylamide, homopolymers and copolymers of derivatives of acrylate and methacrylate, particularly esters and amides having free hydroxyl functionalities including hydrogels, and the like. Inorganic polymers include silicones, glasses, available as Bioglas, and the like. Sols include gold, selenium, and other metals. Particles may also be dispersed water insoluble dyes such as porphyrins, phthalocyanines, etc., which may also act as photosensitizers. Particles may also include diatoms, cells, viral particles, magnetosomes, cell nuclei and the like.

Where the particles are commercially available, the particle size may be varied by breaking larger particles into smaller particles by mechanical means, such as grinding, sonication, agitation, etc.

The particles will usually be polyfunctional or be capable of being polyfunctionalized or be capable of being bound to an sbp member, photosensitizer, or photochemically activatable chemiluminescent compound through specific or non-specific covalent or non-covalent interactions. A wide variety of functional groups are available or can be incorporated. Exemplary functional groups include carboxylic acids, aldehydes, amino groups, cyano groups, ethylene groups, hydroxyl groups, mercapto groups and the like. When covalent attachment of a sbp member, chemiluminescent compound or photosensitizer to the particle is employed, the manner of linking is well known and is amply illustrated in the literature. See for example Cautrecasas, *J. Biol. Chem.*, 245:3059 (1970). The length of a linking group may vary widely, depending on the nature of the compound being linked, the nature of the particle, the effect of the distance between the compound being linked and the particle on the binding of sbp members and the analyte and the like.

The photosensitizer and/or photochemically activatable chemiluminescent compound can be chosen to dissolve in or noncovalently bind to the surface of the particles. In this case these compounds will preferably be hydrophobic to reduce their ability to dissociate from the particle and thereby cause both compounds to associate with the same particle. This possibly can be further reduced by utilizing particles of only one composition that are associated with either the photosensitizer or chemiluminescent compound or by using two types of particles that differ in composition so as to favor association of the photosensitizer with one type of particle and association of the chemiluminescent compound with the other type of particle.

The number of photosensitizer or photochemically activatable chemiluminescent compound molecules associated with each particle will on the average usually be at least one and may be sufficiently high that the particle consists entirely of photosensitizer or photochemically activatable chemiluminescent compound molecules. The preferred number of molecules will be selected empirically to provide the highest signal to background in the assay. In some cases this will be best achieved by associating a multiplicity of different photosensitizer molecules to particles. Usually, the photosensitizer or photochemically activatable chemiluminescent compound to sbp member ratio in the particles should be at least 1, preferably at least 100 to 1, and most preferably over 1,000 to 1.

Photochemically activatable chemiluminescent compound (PACC)—a substance that undergoes a chemical reaction upon direct or sensitized excitation by light or upon reaction with singlet oxygen to form a metastable reaction product that is capable of decomposition with the simultaneous or subsequent emission of light, usually within the wavelength range of 250 to 1200 nm. The term "photoactivatable" includes "photochemically activatable". PACC's that are preferred in the present invention are those that react with singlet oxygen to form dioxetanes or dioxetanones. The latter are usually electron rich olefins (1). Exemplary of such electron rich olefins are enol ethers, enamines, 9-alkylidene-N-alkylacridans, arylvinylethers, dioxenes, arylimidazoles, 9-alkylidene-xanthanes and lucigenin. Other compounds that are included in the term "PACC" include luminol and other phthalhydrazides and chemiluminescent compounds that are protected from undergoing a chemiluminescent reaction by virtue of their being protected by a photochemically labile protecting group, such compounds including, for example,. firefly luciferin, aquaphorin, luminol, etc.

The PACC's of interest will preferably emit at a wavelength above 300 nanometers, preferably above 500 nanometers, and more preferably above 550 nm. Compounds that absorb and emit light at wavelengths beyond the region where the sample components contribute significantly to light absorption will. be of particular use in the present invention. The absorbance of serum drops off rapidly above 500 nm and becomes insignificant above 600 nm; therefore, chemiluminescent compounds that emit light above 600 nm are of particular interest. However, chemiluminescent compounds that absorb at shorter wavelengths are useful when interference absorbance of the sample is absent or when a photosensitizer is used that absorbs longer wavelength light and thereupon activates the chemiluminescent compound.

PACC's of this invention are used as labels and are associated with an sbp member.

The PACC's 1 below generally do not contain allylic CH or NH groups.

The electron rich olefins 1 generally have an electron donating group in conjugation with the olefin:

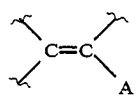 (1)

wherein A is an electron donating group such as, for example, N(D)$_2$, OD, p-C$_6$H$_4$N(D)$_2$, furanyl, N-alkylimidazole, N-alkylpyrrolyl, 2-indoyl, etc., wherein D is, for example, alkyl or aryl, and A is either bound directly to the olefinic carbon or bound by the intermediacy of other conjugated double bonds. The other valencies of the C atoms in olefin 1 are substitutents of 1 to 50 atoms, which may be taken together to form one or more rings, which are fused or unfused, e.g., cycloalkyl, phenyl, 7-norbornyl, naphthyl, anthracyl, acridanyl, adamantyl, and so forth.

Usually there will be no atom bearing a hydrogen atom that is directly attached to the olefin unless that atom is at a position which cannot accommodate a double bond such as at a bridgehead position of a small bicyclic ring system. The more preferred olefins are those that yield a dioxetane that decays rapidly at room temperature (less than 60 minutes, preferably less than 5 minutes, desirably less than 30 sec). The dioxetanes may be luminescent alone or in conjunction with a fluorescent energy acceptor.

Enol ethers 2 generally have the structure:

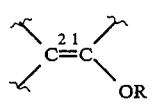 (2)

wherein R is alkyl of 1 to 20 carbon atoms and the remaining substituents on the olefin are selected from the group consisting of H and substituents of 1 to 50 atoms, preferably. Useful enol ether compounds are those with an aryl on the same carbon as the ether where the aryl ring is substituted with an electron donating group at a position that imparts fluorescence. The electron donating group can be, for example, m-hydroxyphenyl, m-dimethylamino-phenyl, 1-(5-aminonaphthyl), pyryl, 1-(3-hydroxypyryl), anthracyl, chrysyl, etc. One or both groups at the 2-position can be aryl where the ketone formed by replacing the 1-carbon with oxygen is fluorescent, for example, β-naphthyl, or 2-anthryl. Exemplary enol ethers by way of illustration and not limitation are:

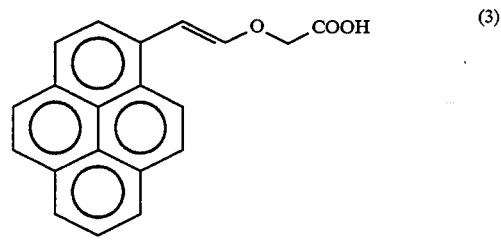 (3)

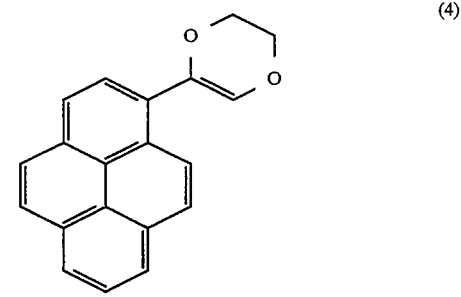 (4)

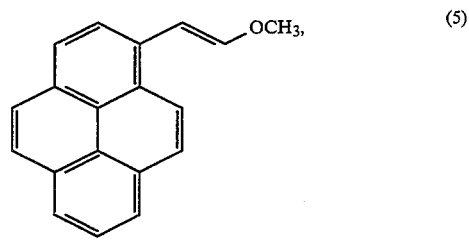 (5)

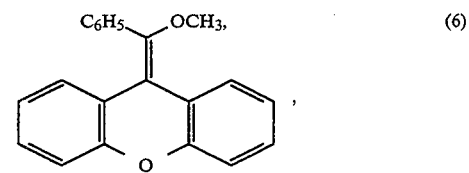 (6)

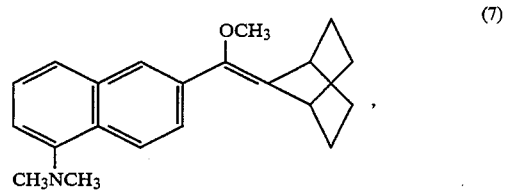 (7)

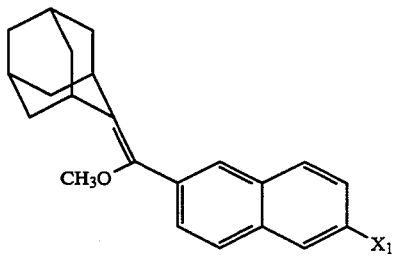

(8)

wherein $X_1$ is H, OC(O)CH$_3$, OCH$_3$, OH, described by Bronstein, et al., in U.S. Pat. No. 4,956,477;

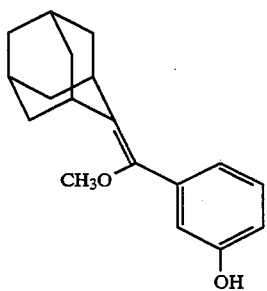

(9)

described by Bronstein, et al., in U.S. Pat. No. 4,956,477;

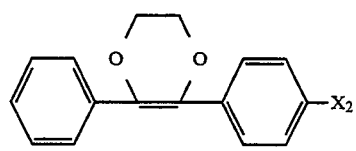

(10)

wherein $X_2$ is H, OH, N(CH$_3$)$_2$, or OCH$_3$, described by P. Schaap, *J. Am. Chem. Soc.*, 104: 3504 (1982) and P. Schaap, *Photochem. and Photobiology* 30:35 (1979);

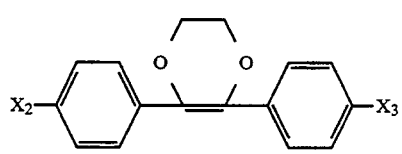

(11)

wherein $X_2$ is defined above, $X_3$ is H, OCH$_3$, or N(CH$_3$)$_2$, described by P. Schaap, Report to U.S. Army Research Office, Oct. 15, 1986, and S. D. Gagnon, Ph.D. Thesis, Wayne State University (1982);

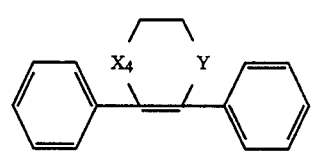

(12)

wherein $X_4$=O, S, CH$_3$N, or PhN and Y=O, S, or CH$_3$N and Ph=phenyl, described by P. Schaap, *Report to Office of Naval Research*, Mar. 17, 1987;

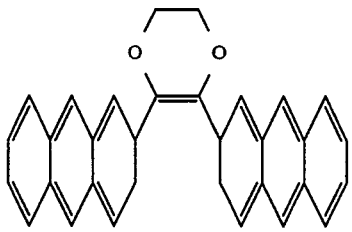

(13)

described by P. Schaap, Report to U.S. Army Research, Oct. 15, 1986;

Enamines 7 generally have the structure:

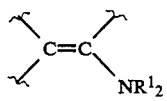

(14)

wherein $R^1$ is independently aryl or alkyl and the remaining substituents on the olefin are selected from the group consisting of H and substituents of 1 to 50 atoms. In general, useful enamines will be governed by the rules set forth above for enol ethers.

Examples of useful enamines, by way of example and not limitation, are the above enol ethers 3–5 with N(CH$_3$)$_2$ in place of OCH$_3$. A further example is

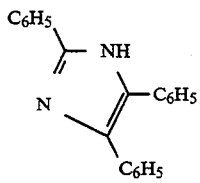

(15)

9-Alkylidene-N-alkylacridans 10 generally have the structure:

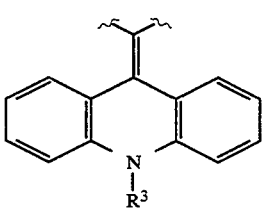

(16)

wherein $R^3$ is alkyl and the remaining substituents on the olefin are selected from the group consisting of H and substituents of 1 to 50 atoms, preferably, phenyl, naphthyl, phenanthryl, m-methoxyphenyl, dimethylamino, trityl, methoxy, N-morpholeno and may be taken together to form a ring such as, for example, adamantyl, N-methacryidanylide, xanthanylidine, 1-(3,4-benzo-5-hydrofurylidene), and the like.

Particular examples of 9-alkylidine-N-alkylacridans useful as labels in the present invention are, by way of illustration and not limitation:

(17)

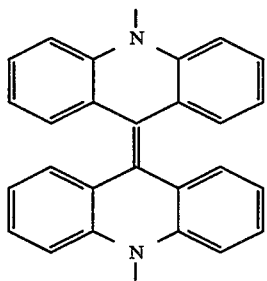

described by Singer, J.Org. Chem. 41, 2685, (1976);

(18)

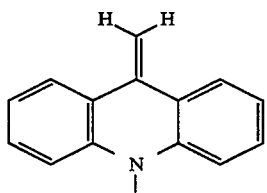

described by E. White, Chem. Letters; , 1491 (1979);

(19)

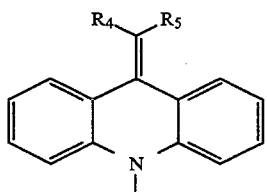

wherein $R_4$ and $R_5$ are independently H or phenyl, described by Singer, et al., J. Am. Chem. Soc. 102: 3823, (1983);

(20)

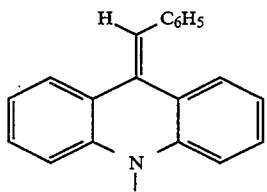

described by McCapra, Chem. Comm; , 944 (1977) and Singer, et al., ibid;

(21)

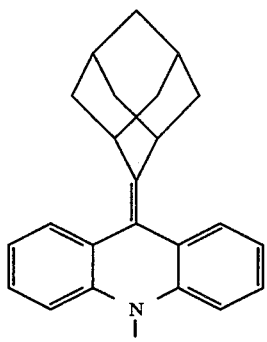

described by McCapra, ibid;

(22)

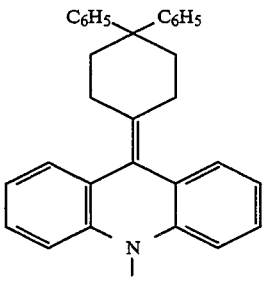

described by McCapra, ibid;

The relevant portions of the above references are incorporated herein by reference.

9-Alkylidene-xanthanes generally have the structure:

(23)

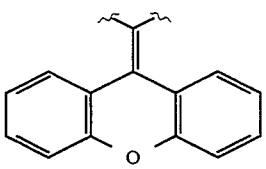

where the substituents on the olefin are selected from the group consisting of H and substituents of 1 to 50 atoms, preferably, phenyl, naphthyl, phenanthryl, m-methoxyphenyl, dimethylamino, trityl, methoxy, N-morpholeno and may be taken together to form a ring such as, for example, admantyl, N-methyacridanylide, xanthanylidine, 1-(3,4-benzo-5-hydrofurylidene), and the like, for example, 9-phenyl-methylidene-xanthene.

Another family of PACC's is 2,3-dihydro-1,4-phthalazinediones. The most popular compound is luminol, which is the 5-amino-6,7,8-trimethoxy and the dimethylaminno[ca]benz analog. It should be noted that luminol has been used as a label in assays; however, excitation of the luminol has been accomplished chemically, not by photoactivation as is the case in the present invention. These compounds are oxidized to the 1,4-phthalazinidiones by singlet oxygen and under subsequent reaction with superoxide or hydrogen peroxide undergo decomposition with light emission.

Another family of PACC's in the 2,4,5-triphenylimidazoles, with lophine as the common name for the parent product. Chemiluminscent analogs include para-dimethylamino and -methoxy substituents.

Other PACC's that satisfy the requirements given above may be found in European Patent Application No. 0,345,776.

Dioxetanes formed by the reaction of singlet oxygen with the chemiluminescent compound have the general structure below where the substituents on the carbon (C) atoms are those present on the corresponding olefin:

(24)

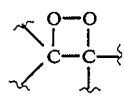

Some of the dioxetanes decompose spontaneously, others by heating, with the emission of light. In some cases the dioxetane is spontaneously converted to a hydroperoxide whereupon base is required to reform the dioxetane and permit decomposition and light emission.

Protected chemiluminescent compounds—are those PACC's that have a photo-removable protecting group. When the protecting group is removed by photoactivation, the compound emits light spontaneously or upon activation with components that are present in the assay medium. Photo-removable protecting groups include, by way of example and not limitation, o-nitrobenzyl, o-acylphenylethyl, alkoxybenzyl, and the like, usually attached to a heteroatom of the PACC.

Exemplary of PACC's that can form part of the protected chemiluminescent compounds are those electron rich olefins mentioned above. Particular examples, by way of illustration, of protected chemiluminescent compounds in accordance with this aspect of the invention are:

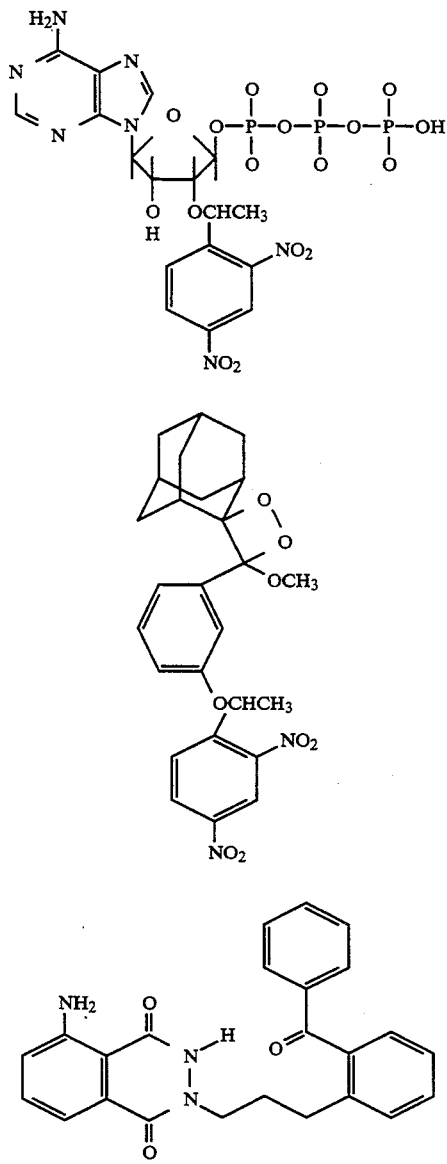

In the case of protected chemiluminescent compounds any necessary reagents will be present prior to photoactivation or photolysis. Such reagents can include enzymes and substrates for such enzymes. In some cases controlling the pH is all that is required. Other agents are alkaline phosphatase, horse radish peroxidase, hydrogen peroxide, etc. Those skilled in the art will appreciate additional reagents upon selection of any appropriate protected chemiluminescent compound guided by the above principles. For example, in the case of compound 1 firefly luciferase and its luciferin substrate may be used. In the case of compound 2, it is only necessary to maintain a basic medium (pH >9). In the case of 2A, hydrogen peroxide and horse radish peroxidase may be used.

Energy acceptor—referred to herein also as fluorescent energy acceptor. A chromophore having substantial absorption higher than 310 nm, normally higher than 350 nm, and preferably higher than about 400 nm. The choice of the energy acceptor will also be governed by the particular PACC. The energy acceptor should be capable of absorbing light emitted by the PACC. Preferably, the absorption maximum of the energy acceptor should be at similar wavelength as the emission maximum of the chemiluminescent compound. A high extinction coefficient is desirable, usually in excess of 10, preferably in excess of $10^3$, and particularly preferred in excess of $10^4$.

A number of different molecules useful as the energy acceptor are described by Ullman, et al. I, II, IV and V, at columns 8 and 9, the relevant portions of which are incorporated herein by reference. Generally, the energy acceptor is a fluorescent compound or fluorescer but energy acceptors that have very weak or no fluorescence are also useful.

One group of fluorescers having a number of the desirable properties described above are the xanthene dyes, which include the fluoresceins derived from 3,6-dihydroxy-9-phenyl-xanthhydrol and rosamines and rhodamines, derived from 3,6-diamino-9-phenylxanthhydrol. The rhodamines and fluoresceins have a 9-o-carboxyphenyl group, and are derivatives of 9-o-carboxyphenyl- xanthhydrol.

These compounds are commercially available with substituents on the phenyl group which can be used as the site for bonding or as the bonding functionality. For example, amino and isothiocyanate substituted fluorescein compounds are available.

Another group of fluorescent compounds are the naphthylamines, having an amino group in the alpha or beta position, usually alpha position. Included among the naphthylamino compounds are 1-dimethylaminonaphthyl-5-sulfonate, 1-anilino-8-naphthalene sulfonate and 2-p-toluidinyl-6-naphthalene sulfonate.

Dye precursors that are activated to react with proteins include 3-phenyl-7-isocyanatocoumarin; acridines such as 9-isothiocyanatoacridine; N-(p-(2-benzoxazolyl)phenyl)maleimide; benzoxadiazoles such as

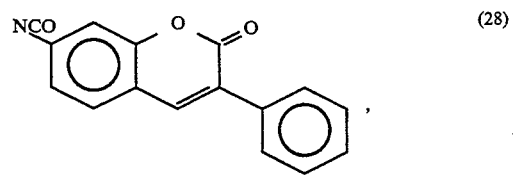

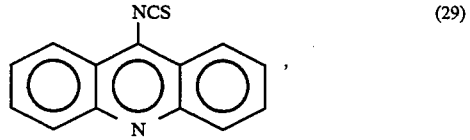

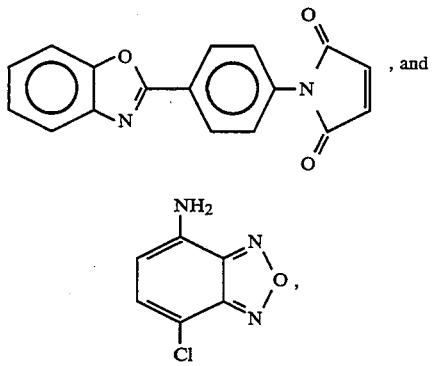

4-chloro-7-nitrobenzo-2-oxa-1,3-diazole; stilbenes, such as 4-dimethylamino-4'-isothiocyanatostilbene and 4-dimethylamino- 4'-maleimidostilbene. Other dyes that can be further functionalized to combine with an sbp member include acridine orange, 7-(p-methoxybenzylamino)-4-nitrobenzo-2-oxa-1,3-diazole; N,N'-dioctadecyloxacarbocyanine p-toluenesulfonate; pyrenes, such as 8-hydroxy-1,3,6-pyrenetrisulfonic acid, and 1-pyrenebutyric acid, merocyanine 540, rose bengal, as well as other readily available fluorescing molecules.

For polynucleotide assays a large variety of energy acceptors can be used, but those that have enhanced fluorescence when bound to double stranded nucleic acids are preferred. Dyes that intercalate such as ethidium bromide and acridine orange are typical examples. A ruthenium derivative developed by Barton (J. Am. Chem. Soc. (1990) 112:4960) is particularly attractive because it is dramatically switched on when intercalated. Alternatively, the energy acceptor may be bound to a second polynucleotide probe that can bind near to the chemiluminescent compound labeled probe or the energy acceptor may be unbound and freely dispersed in solution.

Energy acceptors which are non-fluorescent can include any of a wide variety of azo dyes, cyanine dyes, 4,5-dimethoxyfluorescein, formazans, indophenols, and the like.

Ancillary Materials—Various ancillary materials will frequently be employed in the assay in accordance with the present invention. For example, buffers will normally be present in the assay medium, as well as stabilizers for the assay medium and the assay components. Frequently, in addition to these additives, proteins may be included, such as albumins; organic solvents such as formamide; quaternary ammonium salts; polyanions such as dextran sulfate; surfactants, particularly non-ionic surfactants; binding enhancers, e.g., polyalkylene glycols; or the like.

Wholly or partially sequentially—when the sample and various agents utilized in the present invention are combined other than concomitantly (simultaneously), one or more may be combined with one or more of the remaining agents to form a subcombination. Each subcombination can then be subjected to one or more steps of the present method. Thus, each of the subcombinations can be incubated under conditions to achieve one or more of the desired results.

One aspect of the present invention is a method for determining an analyte. A combination is provided comprising (1) a medium suspected of containing the analyte and (2) a label reagent comprising a first specific binding pair (sbp) member associated with a PACC. Conditions are chosen such that an sbp member complex is formed in relation to the presence of the analyte. For example, the first sbp member may be capable of binding to the analyte or a second sbp member to form a complex related to the presence of the analyte. The method further comprises photochemically activating the PACC and detecting the amount of luminescence generated by the PACC. The amount of luminescence is related to the amount of analyte in the medium.

Generally, the PACC is photo-chemically activated by irradiation with light, which can directly activate the PACC or can activate a photosensitizer, which, upon irradiation, causes molecular oxygen to be converted to singlet oxygen. The singlet oxygen then activates the PACC. The photosensitizer may be bound to a ligand, may be free in solution, or may be bound to a surface depending on the nature of the assay. The product formed by the activation of the PACC with singlet oxygen may decompose spontaneously with emission of light or may be further treated physically or chemically to emit light.

A photosensitizer can be employed in a number of different approaches to produce singlet oxygen, which activates the PACC. The photosensitizer can be employed directly, not being bound to an sbp member. In this approach a relatively large concentration of the photosensitizer is employed, usually at least $10^{-7}$M, preferably at least $10^{-6}$M, most preferably at least $10^{-5}$M. Generally, the amount of photosensitizer employed in this approach is that sufficient to produce a concentration of singlet oxygen that results in activation of the PACC. This approach can be used when the emission of the PACC is substantially modified when a complex is formed or when the amount of PACC in the medium is affected by the presence of the analyte. This will usually be accomplished by separating bound and unbound label. Where a separation is not desired, the emission of the PACC in the complex can be modified by an energy acceptor, which is brought into close proximity to the PACC by binding the energy acceptor to the complex formed as a result of the analyte being present. Where the energy acceptor is fluorescent, the wavelength of the emission is usually modified. When the energy acceptor is not fluorescent, the chemiluminescence will usually be quenched when the PACC becomes bound to the complex.

In a further embodiment of the present invention a photosensitizer and the PACC are partitioned between the bulk solution of the assay medium and a surface as described in the Application. This partitioning will depend upon the amount of analyte present in the sample to be analyzed and the photosensitizer will usually be bound to an sbp member. The photosensitizer molecules that do not become associated with the surface produce singlet oxygen which is unable to reach the PACC before undergoing decay in the aqueous medium. However, when both the photosensitizer and the PACC become associated with the surface by virtue of the formation of a complex resulting from the presence of the analyte, the singlet oxygen produced upon irradiation of the photosensitizer can activate the PACC before undergoing decay. In this method the amount of photosensitizer employed can be considerably less than in the previously described use of the photosensitizer not involving an sbp member bound to the photosensitizer.

As can be seen, the subject assay provides for a convenient method for detecting and measuring a wide variety of analytes in a simple, efficient, reproducible manner, which can employ visual inspection or conventional equipment for measuring the amount of light produced during the reaction.

When the photosensitizer is caused to become associated with the surface as the result of the presence of analyte, it will usually be associated with an sbp member. This may be accomplished in a number of ways. The photosensitizer may contain a functionality for attachment to an sbp member or the sbp member may contain the functionality for attaching to the photosensitizer. The attachment may be accomplished by a direct bond between the two molecules or a linking group can be employed between the sbp member and the photosensitizer. In another embodiment the photosensitizer can be bound to or incorporated in a particle, to which is also attached an sbp member. In both cases the sbp member is capable of binding to the analyte. The photosensitizer can be incorporated into the particle by virtue of being soluble in at least one phase of the particle. The photosensitizer may be bound to the particle when it is not incorporated into the particle. For this purpose the photosensitizer or the particle, or component thereof, is functionalized to provide a means of attaching the photosensitizer and the particle. For particles that are oil droplets or lipid bilayers, the photosensitizer can be bound to the particle by attachment to a long hydrocarbon chain that is compatible with the particle composition. Frequently, at least one, and preferably two, hydrocarbon chains are employed having 8 to 20 or more carbon atoms.

If the particle is a droplet of a fluorocarbon, the photosensitizer may be fluorinated to enhance solubility and reduce exchange and the hydrocarbon chain used for linking will preferably be replaced with a fluorocarbon chain. For silicon particles the photosensitizer may be bound to a polysiloxane. Usually, it will be desirable to minimize the charge and polarity of the photosensitizer so that it resides within the non-aqueous portion of the particle. As mentioned above, the approach involving photosensitizer bound to an sbp member is described fully in the Application.

As mentioned above, the PACC is "associated with an sbp member", and thus functions in the present invention as a label. As used herein, the term "associated with an sbp member" includes the following: Usually, the association of the PACC and sbp member is through covalent binding. However, this label reagent can further comprise a suspendible particle to which the PACC is bound or in which the PACC is non-covalently incorporated. The suspendible particle will also have the sbp member bound to it. This sbp member is generally capable of binding to the analyte or to an sbp member capable of binding to the analyte. When another sbp member is utilized and is also capable of binding to the analyte, a sandwich assay protocol results. The sbp member bound to the PACC can also be analogous to the analyte, in which case a competitive assay protocol can result.

When a photosensitizer is used, the photosensitizer serves to activate the PACC when the medium containing the above reactants is irradiated. The medium is irradiated with light having a wavelength of sufficient energy to convert the photosensitizer to an excited state and render it capable of activating molecular oxygen to singlet oxygen. When bound to an sbp member, the photosensitizer concentration may be very low, frequently $10^{-6}$ to $10^{-12}$M or lower. When the photosensitizer is unbound it will frequently be at a concentration sufficient to absorb an appreciable amount of light, usually at least 0.1%, preferably between 1 and 80%.

The excited state of the photosensitizer will usually be the lowest triplet state and is at least 25 Kcal/mole, preferably at least 23 Kcal/mole, more energetic than the ground state. Generally, the medium is irradiated with light having a wavelength of about 300 to 1200 nm usually 450 to 950, preferably 550 to 800 nm. The period of irradiation will depend on the lifetime of the activated PACC, the light intensity and the desired emission intensity. For short-lived activated PACC's the period may be less than a second, usually about a millisecond but may be as short as a microsecond where an intense flashlamp or laser is used. For longer-lived activated PACC's the irradiation period can be longer and a less intense steady light source can be used. In general, the integrated light intensity over the period of irradiation should be sufficient to excite at least 0.1% of the photosensitizer molecules, preferably at least 30%, and most preferably every, photosensitizer molecule will be excited at least once.

The luminescence or light produced in any of the above approaches can be measured visually, photographically, actinometrically, spectrophotometrically or by any other convenient means to determine the amount thereof, which is related to the amount of analyte in the medium.

A helium-neon laser is an inexpensive light source for excitation at 632.6 nm. Photosensitizers that absorb light at this wavelength are compatible with the emission line of a helium-neon laser and are, therefore, particularly useful in the present invention. Other light sources include, for example, other lasers such as Argon, YAG, He/Cd, and ruby; photodiodes; mercury, sodium and xenon vapor lamps; incandescent lamps such as tungsten and tungsten/halogen; and flashlamps.

Another aspect of the invention is a method for determining an analyte, which comprises (a) combining in an assay medium either simultaneously or wholly or partially sequentially (1) a medium suspected of containing an analyte, (2) a label reagent comprising a first member of a specific binding pair (sbp member) bound to a compound capable of chemiluminescence upon reaction with singlet oxygen, and (3) an insolubilized reagent comprising a fluorescent energy acceptor bound to, or capable of becoming bound to, a second sbp member under conditions wherein an sbp member complex involving said label reagent is formed in relation to the presence of analyte in said medium and energy from said chemiluminescent compound is capable of activating said fluorescent energy acceptor, (b) activating said compound with light, and (c) examining said assay medium for a signal, the presence or intensity thereof being related to the amount of analyte in said medium.

The method and compositions of the invention may be adapted to most assays involving sbp members such as ligand-receptor, e.g., antigen-antibody reactions, polynucleotide binding assays, and so forth. The assays may be homogeneous or heterogeneous, competitive or sandwich. In a homogeneous assay approach, the sample may be pretreated if necessary to remove unwanted materials. The immunological reaction for a sandwich type assay usually involves an sbp member, e.g., an antibody, that is complementary to the analyte and bound to the PACC, a second sbp member, e.g., antibody, that is also complementary to the analyte, and the sample of interest. In a competitive protocol the PACC may be associated with an sbp member that is analogous to, usually a derivative of, the analyte or with an sbp member complementary to the analyte, e.g., an antibody.

The PACC may be utilized either by itself or associated with an energy acceptor. The ability of luminescence produced by an activated PACC to activate the energy acceptor may be governed by the binding of the two sbp members or may be the consequence of a relatively high concentration of the energy acceptor in the vicinity of the activated PACC, wherein the concentration will usually be at least micromolar, usually at least millimolar. When the PACC is bound to an sbp member, its concentration, by contrast, may be quite low, often $10^{-5}$ to $10^{-15}$, usually $10^{-8}$ to $10^{-14}$ and detection of the extent thereof may be carried out in a homogeneous solution without separation provided only that the luminescent intensity is modified when the PACC is in a binding complex.

In a heterogeneous assay approach, a sample suspected of containing an analyte, which is an sbp member, is combined with a reagent that is comprised of a complementary sbp member bound to a support, which may be a surface or a particle having the PACC. An energy acceptor associated with another sbp member may also be employed wherein the sbp member is either complementary to (sandwich) or analogous to (competitive) the analyte. These materials are generally combined either simultaneously or wholly or partially sequentially. The support is then separated from the liquid phase and either the solid phase or the liquid phase is examined for the presence of luminescent energy, usually by irradiating the particular phase in question and measuring the amount of light emitted.

An assay for the analyte will normally be carried out in an aqueous buffered medium at a moderate pH, generally that which provides optimum assay sensitivity. As explained above, the assay can be performed either without separation (homogeneous) or with separation (heterogeneous) of any of the assay components or products.

The aqueous medium may be solely water or may include from 0.01 to 80 or more volume percent of a cosolvent. The pH for the medium will usually be in the range of about 4 to 13, more usually in the range of about 5 to 10, and preferably in the range of about 6.5 to 9.5. The pH will usually be a compromise between optimum binding of the binding members and the pH optimum for other reagents of the assay such as members of the signal producing system. For example, the activated PACC may require a certain pH range in order to decay to produce luminescence.

Various buffers may be used to achieve the desired Ph and maintain the pH during the determination. Illustrative buffers include borate, phosphate, carbonate, tris, barbital and the like. The particular buffer employed is not critical to this invention, but in an individual assay one or another buffer may be preferred.

Moderate temperatures are normally employed for carrying out the assay and usually constant temperature, preferably, room temperature, during the period of the measurement. Incubation temperatures will normally range from about 5° to 99° C., usually from about 15° to 70° C. more usually 20° to 45° C. Temperatures during measurements will generally range from about 10° to 70° C., more usually from about 20° to 45° C., more usually 20° to 25° C. In some instances the activated PACC may require heating up to 100° C. in order to decay to produce luminescence.

The concentration of analyte which may be assayed will generally vary from about $10^{-5}$ to $10^{-17}$M, more usually from about $10^{-6}$ to $10^{-14}$M. Considerations, such as whether the assay is qualitative, semiquantitative or quantitative, the particular detection technique and the concentration of the analyte of interest will normally determine the concentrations of the various reagents.

While the concentrations of the various reagents in the assay medium will generally be determined by the concentration range of interest of the analyte, the final concentration of each of the reagents will normally be determined empirically to optimize the sensitivity of the assay over the range. That is, a variation in concentration of the analyte which is of significance should provide an accurately measurable signal difference.

While the order of addition may be varied widely, there will be certain preferences depending on the nature of the assay. The simplest order of addition particularly for a homogeneous assay is to add all the materials simultaneously. Alternatively, the reagents can be combined wholly or partially sequentially. Optionally, an incubation step may be involved after the reagents are combined, generally ranging from about 30 seconds to 6 hours, more usually from about 2 minutes to 1 hour.

In a homogeneous assay after all of the reagents have been combined, they can be incubated, if desired. Then, the combination is irradiated and the resulting light emitted is measured. The emitted light is related to the amount of the analyte in the sample tested. The amounts of the reagents of the invention employed in a homogeneous assay depend on the nature of the analyte.

The following assays are provided by way of illustration and not limitation to enable one skilled in the art to appreciate the scope of the present invention and to practice the invention without undue experimentation. It will be appreciated that the choice of analytes, photosensitizers, PACC's, surfaces, particles and reaction conditions will be suggested to those skilled in the art in view of the disclosure herein and the examples that follow.

In the following assays, components are combined in a predominantly aqueous medium of pH 6 to 8.5.

A. In an assay for HCG a urine sample is combined with (1) antibody to HCG bound to 1 micron latex particles and (2) an antibody against a separate non-overlapping epitope of HCG bound to the PACC 4After incubation of the suspension for 30 minutes, the particles are separated from the medium by centrifugation, washed and irradiated with 300 nm light. The intensity of light emitted following the irradiation is related to the amount of HCG in the sample. The separated particles can be irradiated directly, or suspended in an aqueous or non-aqueous solvent prior to irradiation.

B. In a procedure for the assay of HCG in serum similar to A, the latex beads that are used are stained with the photosensitizer, copper phthalocyanine, and, following incubation, are separated from the medium and then irradiated with 600 nm light. The intensity of the emitted light is related to the amount of HCG in the sample.

C. In an assay for digoxin in serum, the PACC, luminol, conjugated to digoxigenin is incubated with the sample in a polystyrene well that has been stained with tetradecylphthalocyanine. The surface of the well is coated with an antibody to digoxin. After incubation for 30 minutes and removal of the assay medium, the well is irradiated with 600 nm light. It is preferable to add an alkaline solution prior to irradiation (pH 10–12). The intensity of the light emitted following irradiation is inversely related to the concentration of digoxin in the sample.

D. In an assay for albumin in urine, the sample is combined with (1) an antibody to albumin labeled with the PACC and (2) an antibody to albumin directed against a non-overlapping albumin epitope that is labeled with energy acceptor,

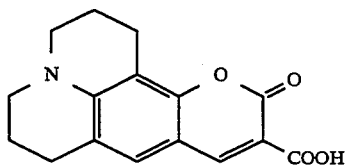

(32)

The photosensitizer, methylene blue, is included in the assay medium. The medium is incubated for 10 minutes and then irradiated with 600 nm light. The intensity of the light emitted by the energy acceptor (about 500 nm) following termination of irradiation is directly related to the amount of albumin in the sample.

E. In an assay for thyroxine in serum, the sample is combined with thyroxine bound to latex beads, into which has been incorporated the PACC 10 wherein $X_2$ is $N(CH_3)_2$. Antibody to thyroxine bound to the sensitizer, rose bengal, is included in the assay medium. Following incubation for 10 minutes, the medium is irradiated with 550 nm light and the light emitted following termination of the irradiation is measured. The emitted light intensity is inversely related to the amount of thyroxine in the sample.

F. In an assay for a target polynucleotide sequence in a sample containing DNA, a 25-base oligonucleotide complementary with the target sequence and conjugated to PACC 23. which is 9-phenylmethylidene xanthane is mixed with the sample. The medium is then heated to 75° C. and cooled to 55° C. to permit hybridization of the oligonucleotide to any target sequence present. The energy acceptor and intercalator, acridine orange, and the photosensitizer, phthalocyanine tetrasulfonic acid, are present in the hybridization solution or may be added following completion of the hybridization reaction. The solution is then irradiated with 600 nm light and the intensity of light emitted by the acridine orange (about 500 nm) following termination of the irradiation is measured. The light intensity is directly related to the presence of the target sequence.

G. In an assay for a target polynucleotide sequence in a sample containing DNA, a 25-base oligonucleotide complementary to the target sequence and labeled with the photosensitizer, phthalocyanine, is caused to hybridize to the target as in F above. A compound that binds to the minor groove of double stranded DNA, Hoechst dye 33258, which is attached to PACC 20, N-methyl-9-phenylmethylidene acridan, is included in the medium or added following hybridization. The medium is then irradiated with 600 nm light and the light emitted following termination of the irradiation is measured. The emitted light intensity is directly related to the amount of target sequence present in the sample.

H. In an assay for hepatitis B surface antigen (HBsAg) in serum, the sample is combined with (1) 150 nm latex particles stained with the PACC, and coated with antibodies to HBsAg, and (2) 150 nm latex beads stained with the photosensitizer tetraphenyl porphyrin, and coated with antibodies to HBsAg. After incubation of the mixture for one hour, the suspension is irradiated with 550 nm light. Following termination of the irradiation, the emitted light intensity is measured and related to the amount of HBsAg in the sample.

I. In an assay for HBsAg in whole blood, procedure H is followed except that the latex beads containing the PACC are replaced with latex beads stained with PACC 23, which is 9-phenylmethylidenexanthane and the energy acceptor

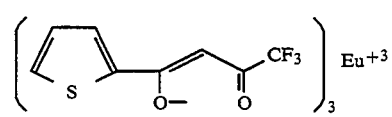

(33)

The intensity of light emitted at 610 to 620 nm is measured and related to the concentration of HBsAg in the sample.

Another aspect of the present invention relates to kits useful for conveniently performing the assay method of the invention for determining the presence or amount of an analyte in a sample suspected of containing the analyte. To enhance the versatility of the subject invention, the reagents can be provided in packaged combination, in the same or separate containers, so that the ratio of the reagents provides for substantial optimization of the method and assay. The reagents may each be in separate containers or various reagents can be combined in one or more containers depending on the cross-reactivity and stability of the reagents. The kit comprises (1) a composition comprising a PACC bound to an sbp member. The kit can also include one or more additional sbp member reagents and optionally a photosensitizer. An energy acceptor can be attached to an sbp member to form a reagent or it can be provided by itself as a reagent. An sbp member that is bound to a surface can also be included. The kit can further include other separately packaged reagents for conducting an assay including ancillary reagents, and so forth.

EXAMPLES

The invention is demonstrated further by the following illustrative examples. Parts and percentages used herein are by weight unless otherwise specified. Temperatures are in degrees centigrade (°C.).

Abbreviations $Ab_F$ - Mouse monoclonal antibody to fluorescein.

$Ab_{IF}$ - Mouse monoclonal antibody to intrinsic factor.

$B_{12}$-$LC_{25}$-F - Vitamin $B_{12}$ linked to carboxy fluorescein (F) by means of a linking group 25 atoms in chain length, namely,

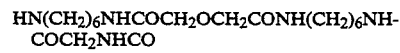

$BA$-$C_{18}$ - 4-(N,N-Dioctadecylcarboxamidomethoxy)-benzal acridan t-Bu - tert-butyl TFA - trifluoroaetic acid

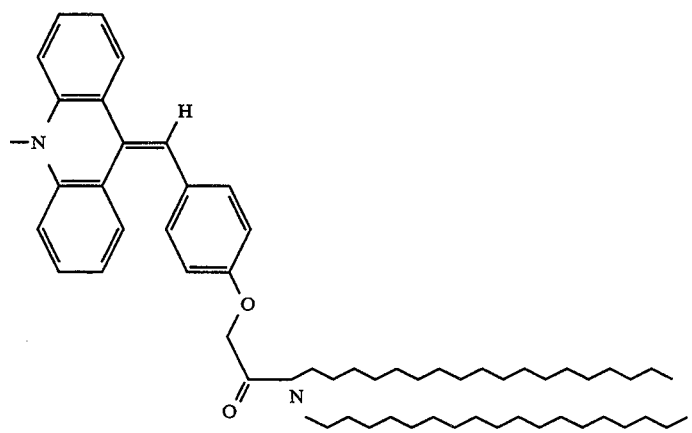

Biotin-LC$_{21}$-F

F-LC$_{21}$NH$_2$ - carboxyfluorescein to which is bound

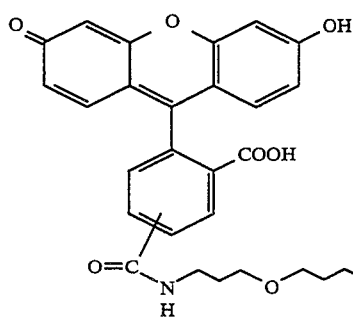

BSA - Bovine serum albumin
Chl-a - Chlorophyll-a the linking group HN(CH$_2$)$_6$NHCOCH$_2$OCH$_2$CONH(CH$_2$)$_6$NH$_2$ HCG - Human chorionic gonadotropin
Lip - Liposome
nC$_{10}$ - tetra-(n-decyl)phthalocyanin aluminum chloride complex.

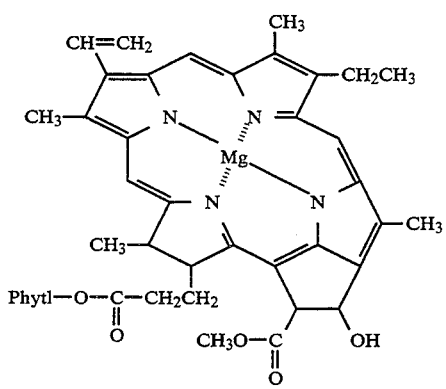

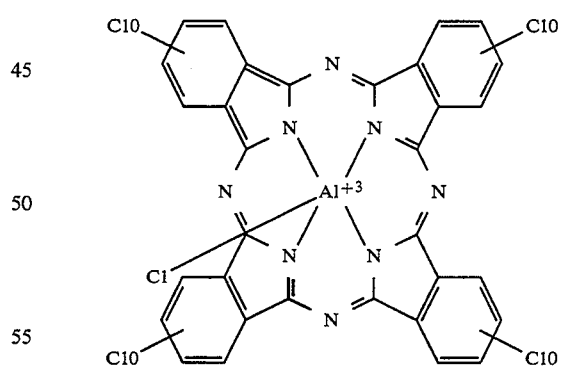

D-H$_2$O - dionized water
DPPC - dipalmitoylphosphatidyl choline
DPPG - dipalmitoylphosphatidyl glycerol
DPPE - dipalmitoylphosphatidyl ethanolamine
EDAC - 1-Ethyl-3-(3-Dimethylaminopropyl) carbodiimide hydrochloride.

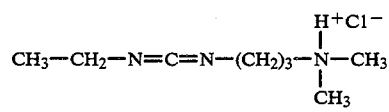

F - Fluorescein
F-NHS - the N-hydroxy succinimide ester of 6-carboxy fluorescein OD - Oil droplet
OD/BA-C$_{18}$ - Oil droplets containing BA-C$_{18}$
PB - Polystyrene beads
PB/BA-C$_{18}$ - PB containing di-octadecylamino-carboxylbenzal acridan
PB/nC$_{10}$ - PB containing tetra-(n-decyl)aluminum phthalocyanin
PBS - phosphate buffered saline 0.02M NaPi, 0.14M NaCl/pH 7.2
Pi - Phosphate
Sulfo-NHS - Sulfo-N-hydroxysuccinamide TSH - Thyroid stimulating hormone or thyrotropic hormone SATA - S-acetylthioglycolic acid N-hydroxysuccinimide ester RLU - Relative light units.

$Ab_1$ ($\alpha HCG$) - monoclonal anti-HCG$\beta$ antibody 12A8

$Ab_2$ ($\beta HCG$) - monoclonal anti-HCG$\alpha$ antibody 9D7

$Ab_1$ ($\beta TSH$) - monoclonal anti-TSH$\beta$ antibody 35

$Ab_2$ ($\beta TSH$) - monoclonal anti-TSH$\beta$ antibody-9G3

NHS - N-hydroxysuccinimide

IF - intrinsic factor

DMSO - dimethyl sulfoxide avidin-PB/BA-C18 - PB/BA-$C_{18}$ covalently bound to avidin $Ab_F$-PB/nC10 - PB/n$C_{10}$ coated with $Ab_F$ DMF - dimethyl formamide DCC - dicyclohexylcarbodiimide TEA - triethylamine TLC - thin layer chromatography TNBSA - 2,4,6-trinitrobenzenesulfonic acid Dig-CMO - O-carboxymethyloxime of digoxigenin-3-one BGG - bovine gamma globulin Biotin-$LC_7$-NHS - sulfosuccinimidyl-6-(biotinamido)hexanoate All monoclonal antibodies were produced by standard hybrid cell technology. Briefly, the appropriate immunogen was injected into a host, usually a mouse or other suitable animal, and after a suitable period of time the spleen cells from the host were obtained. Alternatively, unsensitized cells from the host were isolated and directly sensitized with the immunogen in vitro. Hybrid cells were formed by fusing the above cells with an appropriate myeloma cell line and culturing the fused cells. The antibodies produced by the cultured hybrid cells were screened for their binding affinity to the particular antigen, e.g. TSH or HCG. A number of screening techniques were employed such as, for example, ELISA screens. Selected fusions were then re-cloned.

EXAMPLE 1

Assay for Vitamin $B_{12}$

Preparation of $B_{12}$-$LC_{25}$-F Conjugate $B_{12}$-$LC_{25}$-F conjugate with a spacer arm of 25-atoms long (see below) was prepared by introducing carboxylic groups in the $B_{12}$ molecule by reacting with the $B_{12}$ molecule with methylisocyanatoacetate (which reacts with the hydroxyl group of ribose in the $B_{12}$ molecule forming a stable carbamate bond), followed by base hydrolysis of methyl ester to generate the carboxylic group. The introduced carboxylic group at the 5'-OH site was converted into the NHS ester of $B_{12}$ and then reacted with the fluorescein amine F-$LC_{12}$-$NH_2$ to generate the final product $B_{12}$-$LC_{25}$-F.

A. Synthetic scheme for 21 atom chain on 5-carboxy fluorescein.

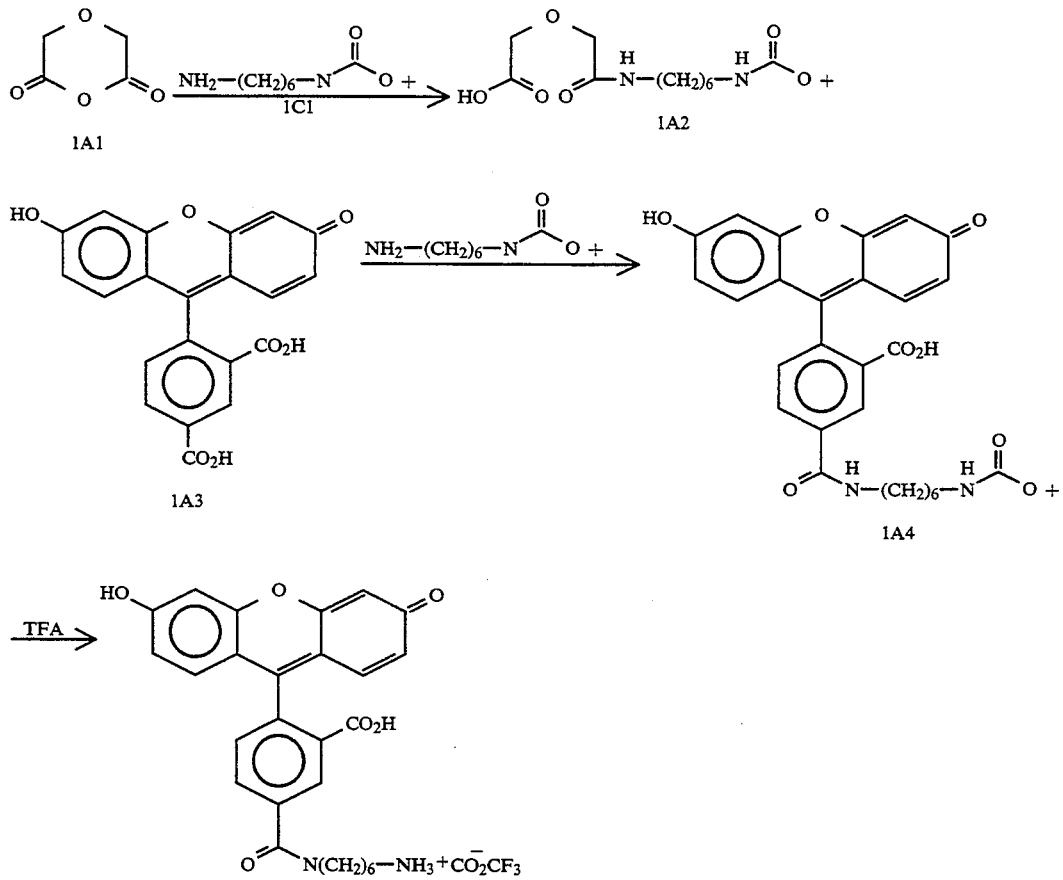

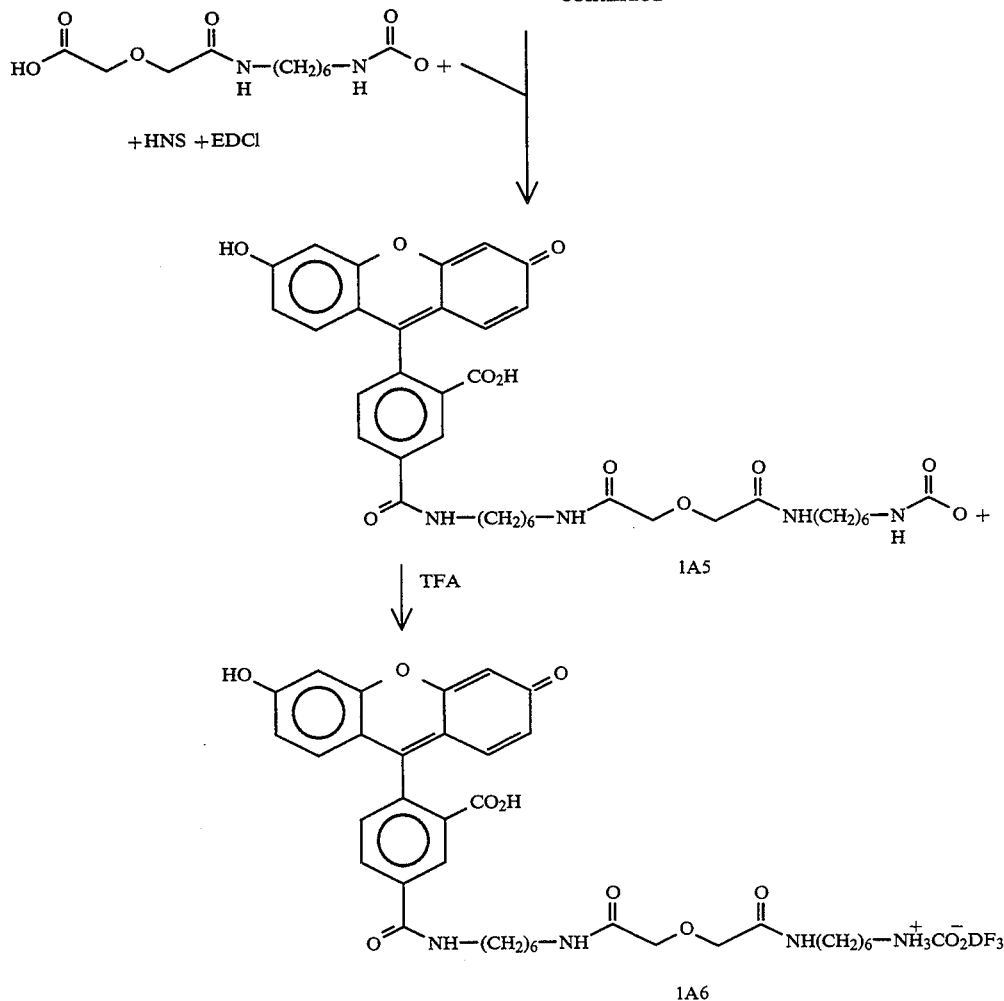

1.2 g (0.0056 mols) of the monoprotected diamine 1C1 was dissolved in 25 mL of anhydrous dichloromethane and to this stirring solution was added 0.64 g (0.0056 mols) diglycolic anhydride 1A1 and the reaction was left 5 hr at ambient temperature. The reaction mixture was concentrated and extracted with 50 mL water, 50 mL ethyl acetate. The organic phase was washed with 0.1N HCl (50 mL), water (2×50 mL) and dried with MgSO₄ and concentrated in vacuo to yield 1.35 g 1A2.

$^1$H NMR 100 MHz (CD₃OD) δ 4.0,3.85(2S,4,O—CH₂—CO) δ 3.0,2.82 (2t,4,NCH₂), δ 1.4 (S, CH₃), 500 mg (1.33 mmols) of 5-carboxyfluorescein, 1A3, (dried 80° over P₂O₅, in vacuo 0.05 mm, 16 hr.) was dissolved in 20 ml anhydrous dimethylformamide. To the stirring solution was added 280 mg (1.46 mmols) of 1-ethyl-3-dimethylaminopropylcarbodiimide and 168 mg (1.46 mmols) of N-hydroxysuccinimide. After stirring for 16 hr., 400 mg (1.85 mmols) of mono t-Boc 1,6-diaminohexane was added, and the mixture was stirred for an additional 4 hours at ambient temperature. The resulting mixture was concentrated to a thick solution and dissolved in 1:9 methanol-ethylacetate (100 mL) and extracted with water (3×50 ml), 0.1N HCl (100 ml). The organic phase was dried over MgSO₄ and evaporated in vacuo. The residue was purified on Analtech 1000μ, 20×20 cm silica gel GF plates using 0.5% acetic acid and 10% methanol in dichloro-methane. The pure bands were pooled and extracted with (1:1) methanol/dichloromethane, concentrated, and the residue was dissolved in the minimum of methanol and added dropwise into water. The mixture was then centrifuged and the solid dried in vacuo, yielding 83% of 1A4.

3.5g (0.0064 mols) of mono tBoc 1,6-diaminohexyl-5-carbonyl fluorescein 1A4 (dried 90° C., over P₂O₅ in vacuo 0.05 mm 16 hr.) was treated with 40 ml dichloromethane/trifluoroacetic acid 1/1. The solution was swirled in an ice bath and after 5 minutes the solvent was evaporated and the crude residue was dried in vacuo overnight.

42 mg of mono-t-Boc 1,6-diaminohexylglycolic acid amide 1A2, 22 mg (0.190 mmols) N-hydroxysuccinimide, and 36.4 mg (0.190 mmols) 1-ethyl-3-(3-dimethylaminopropyl) carbodiimide were combined in 4 mL anhydrous dichloromethane and stirred at ambient temperature 16 hours. The solution of the activated acid was added dropwise into a stirring solution of 75 mg (0.127 mmols) of the above 1,6-diaminohexyl-5-carboxyl fluorescein derivative, 10 ml anhydrous dimethylformamide and 66 ml triethylamine. After 1 hour the reaction was taken up in water and extracted with ethyl acetate. The organic phase was washed with water (3×25 mL), dried with MgSO₄, concentrated and purified on one 20×20 cm 1000μ Analtech silica gel GF plate 10% methanol, 0.5% acetic acid in dichloromethane. The pure band was isolated, extracted with methanol/dichloromethane, concentrated and dried in vacuo. The residue was taken up into 4 mL methanol and added dropwise to swirling 0.1N HCl (8 mL), centrifuged and dried, 84 mg 1A5, 84% yield.

1H NMR 500 MHz(CD$_3$OD) δ 8.4(d,1,ArH,J=0.71 Hz) δ 8.17 (dd,1,ArH,J=8.0 Hz) δ 7.3(d,1,ArH,J=8.0 Hz) δ 4.04 (d,4,O—CH$_2$—CO) δ 1.41 (S,9,3CH$_3$).

Anal. Calc for C$_{42}$H$_{52}$N$_4$O$_{11}$: C, 63.7;H,6.8;N,7.0. Found: C,63.56;H,6.64;N,7.0.

To the above tBoc-21-atom long chain amine of 5-carboxyfluorescein (dried 80° C. over P$_2$O$_5$ in vacuo, 0.05 mm) was added 5 ml trifluroacetic acid at ambient temperature. After 5 min the acid was evaporated and then dried 80° C. in vacuo to yield the trifluoracetic acid salt 1A6.

FAB-MS C$_{37}$H$_{44}$N$_4$O (M+H)+ 689.

B. Synthetic scheme for modification of B$_{12}$ at 0.5$^1$ position of the ribose ring with a 25 atom spacer linked to 5-carboxyl fluorescein.

purified on Whatman PLC$_{18}$F preparative plate 1000μ 20×20 cm eluant 2:8 isopropanol-water containing 0.5 ml acetic acid +1 g NaCl per 100 ml. Rf=0.625 Isolation from absorbant gave the methyl ester 1B$_2$.

(+) -FABM5 (C$_{67}$H$_{93}$CoN$_{15}$O$_{17}$P) mw 1469.6; (M+H) 1470, (M-CN)+ 1444.

40 mg (0.0272 mmols) of the B$_{12}$O5'-carbonyl glycine methyl ester 1B$_2$ was taken up in 2.5 ml 2/1 methanol-water, pH adjusted to 9.5 with ammonium hydroxide and stirred for 16 hours at ambient temperature.

tlc analysis Whatman KC$_{18}$F; 2:8 isopropanol-water, 0.5% acetic acid, 1% NaCL Rf=0.79.

The reaction mixture was concentrated to dryness and the product isolated using two Whatman PLC$_{18}$F plates 1000μ, 20×20 cm eluant same as above. The pure band was extracted with methanol, the extract was concentrated, dissolved in 2:7 methanol-dichloromethane, filtered and concentrated. The residue was dissolved in 4 ml methanol and added dropwise to 4 ml ethyl ether. The precipitate was centrifuged and dried

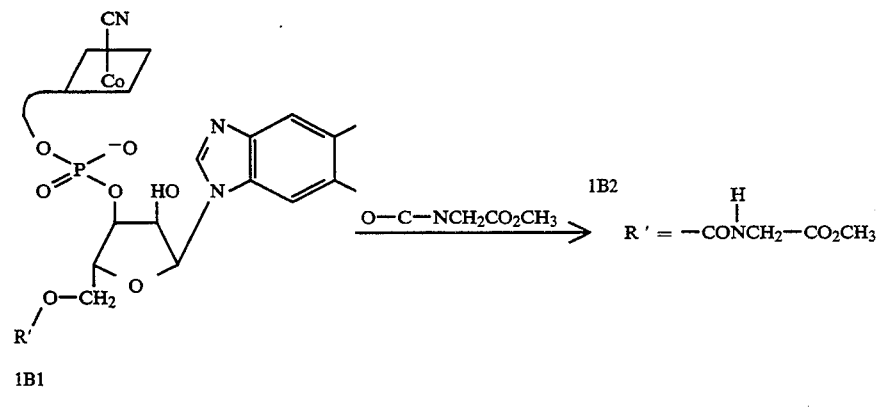

1B1
R' = H

1B2
CH$_3$OH/NH$_4$OH

1B3
R' = —CONCH$_2$CO$_2$H
         H

1B3
1) NHS/EDCl
2) 1A6, (C$_2$H$_5$)$_3$N

1B4

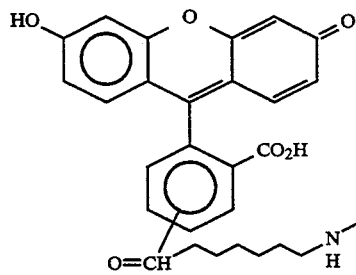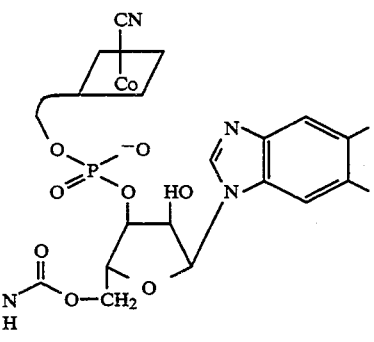

25 mg (0.0185 mmols) of vitamin B$_{12}$ (1B$_1$) (dried 48 hours 80°, 10μ) was dissolved in 1.25 ml anhydrous dimethylsulfoxide. To this stirring solution was added 21.2 mg (0.185 mmols) methyl isocyanatoacetate and reaction was then left 24 hours at ambient temperature. The reaction mixture was added dropwise into a 10 ml stirring ethylacetate solution. The precipitated product was centrifuged, then resuspended in a minimum amount methanol and reprecipitated. This material was at 60° C. over P$_2$O$_5$, 0.5 mm, 16 hours, to yield 28 mg product 1B$_3$.

(+)-FAB-MS(C$_{66}$H$_{91}$CoN$_{15}$O$_{17}$P) mw 1455.7, (M+H)+ 1456, (M-CN)+ 1431.

15 mg (0.013 mmols) of B$_{12}$O5'-carbonyl glycine 1B$_3$, 3.66 mg (0.016 mmols) N,N-dicyclohexyl carbodiimide, 1.95 mg (0.017 mmols) N-hydroxy succinimide were combined with 5 ml anhydrous dimethyl formamide and stirred at ambient temperature for 16 hours. The reaction mixture was added dropwise to a stirring solution of 13.6 mg (0.17 mmols) 21-atom long chain amine of 5-carboxyfluorescein 1A6 in 2.02 mg (0.02 mmols) triethylamine in 4 ml dry dimethylformamide, and stirred 12 hours at ambient temperature.

The crude reaction was concentrated under vacuum at 40° C. and residue taken up in 2 ml methanol and precipitated with 6 ml ethyl ether and centrifuged. The solid was purified on Whatman PLC$_{18}$F plate 1000μ 20×20 cm, eluant 7:3 methanol-water, 0.5% acetic acid $_2$Rf~0.78, 37% yield 1B$_4$.

(+)-FAB-MS ($C_{103}H_{133}CoN_{19}O_{25}P$), (M+H)+ 2125; (M-CN)[21] UV/max 360 (ε 26,600), 50 (ε 57,000), 550(ε 9500).

II. Biotinylation of Anti-Intrinsic Factor (Ab$_{IF}$) Antibodies

The monoclonal anti-intrinsic factor antibodies (Ab$_{IF}$) were prepared by standard hybrid cell technology based on that reported by Kohler and Milstein in *Nature* 256(1975) 495–497.

Using biotin-LC$_7$-NHS from Pierce Chemical Co., Rockford, Ill., three different levels of biotinylations (Ab$_{IF}$:biotin in reaction mixture=1:10, 1:50, or 1:200) were performed. The Ab$_{IF}$ was in 0.05M NaPi, 0.05M NaCl/pH=7.8 at [IgG]=2.5 mg/ml. To this solution DMSO (1% of the total volume) containing the required amount of biotin-LC$_7$-NHS was added and then the solution was incubated overnight at 4° C. Finally, the reaction mixtures were purified on Sephadex® G25 and extensively dialyzed against 0.05M NaPi, 0.02% NaN$_3$/pH=7.2. The biotinylated anti-intrinsic factor antibodies were stored frozen.

III. Preparation of Particles

A. Materials 175 nm carboxylate modified latex: Bangs Laboratories, Inc. Carmel, Ind. 46032.

38 nm carboxylate modified latex: Duke Scientific Corporation, Palo Alto, Calif. 94303.

Ethylene glycol, benzyl alcohol, benzonitrile Aldrich Chemical Co.

Sephadex® G-25: Pharmacia.

nC$_{10}$: Ultra Diagnostics Corporation, Seattle, Wash. 98105.

B. AbF-PB/nC$_{10}$ 1. 38 nm diameter particles

A 2.1 mM solution of nC$_{10}$ was prepared in benzyl alcohol. Ethylene glycol (16 mL) was placed in a 20 mL glass vial and warmed to 100° on a laboratory hot plate. Benzyl alcohol (1.6 mL) was added and the mixture stirred magnetically. Stock latex suspension (2 mL, 38 nm carboxylate modified latex containing 10% solids) was added and the mixture allowed to equilibrate for 3 to 4 minutes. The nC$_{10}$ solution (0.4 mL) was added slowly in 100 mL aliquots. Heating at 100° was continued for 5 minutes; then the mixture was allowed to cool to room temperature. After cooling, the mixture was applied to a column of Sephadex G-25 (2.5×15 cm) equilibrated with 50% aqueous ethanol. The latex containing fractions were pooled and applied to a second Sephadex G-25 column (2.5×35 cm) equilibrated with water. The latex was eluted in a volume of 30 mL.

2. 175 nm diameter particles

A 2.1 mM solution of nC$_{10}$ was prepared in benzyl alcohol. Ethylene glycol (80 mL) was placed in a 125 mL Erlenmeyer flask and warmed to 110° on a laboratory hot plate. Benzyl alcohol (8 mL) was added and the mixture stirred magnetically. The nC$_{10}$ solution (2 mL) was added followed immediately by stock latex suspension (10 mL, 175 nm carboxylate modified latex containing 10% solids). Heating was continued at 100° to 110° for 10 minutes while stirring vigorously. The flask was then placed in a room temperature water bath to cool. After cooling, the mixture was diluted with an equal volume of ethanol and immediately centrifuged at 15,000 rpm (Sorval, SA 600 rotor) for two hours. The faintly blue supernatant was decanted and the pellet resuspended in 50% aqueous ethanol (20 mL) using a bath sonicator to disperse the particles. Centrifugation was repeated, 15,000 rpm 1 hour. The supernatants were decanted and the pellet resuspended in water. Following a final centrifugation, the pellets were resuspended in water to a final volume of 20 mL.

3. Binding of the beads to Ab$_F$ is described in Example 3, paragraph V.

C. Avidin-PB/BA-C$_{18}$ 175 nm diameter particles

A 10 mM solution of the dioctadecylbenzalacridan (BA-C$_{18}$) was prepared in benzonitrile. Ethylene glycol (80 mL) was placed in a 125 mL Erlenmeyer flask and warmed to 100° on a laboratory hot plate. Benzonitrile (9 mL) was added and the mixture stirred magnetically. The BA-C$_{18}$ solution (1 mL) was added followed immediately by stock latex suspension (10 mL, 175 nm latex containing 10% solids described above). Heating was continued at 100° for 5 minutes while stirring vigorously. The flask was then placed in a room temperature water bath to cool. After cooling, the mixture was diluted with an equal volume of 50% aqueous ethanol and immediately centrifuged at 15,000 rpm (Sorval, SA 600 rotor) for a total of 4 hours. The supernatant was decanted and the pellet resuspended in aqueous ethanol using a bath sonicator to disperse the particles. Centrifugation was repeated, 15,000 rpm 1 hour. The supernatants were decanted and the pellet resuspended in water. Following a final centrifugation, the pellets were resuspended in water to a final volume of 20 mL.

Binding of the beads to avidin is described in Example 3, paragraph VI.

IV. Assay Protocol

The assay was performed by mixing 100 μl of B$_{12}$ calibrators (diluted from an original 10 μg/ml B$_{12}$ stock solution 10 μM KCN) in assay buffer (0.05M KPi, 0.1% BSA, pH 7.5, BSA was free of B$_{12}$ and B$_{12}$ binder) with 50 μl of 2.2 ng/ml B$_{12}$-LC$_{25}$-F and 50 μl of premixed 88 ng/ml intrinsic factor (IF), 8.8 μg/ml Ab$_{IF}$-biotin. These mixtures were incubated at room temperature for 15 minutes in the dark; then 0.75 ml of 0.05 Tris-HCl, 0.05 NaPi, 0.15M NaCl, 0.1% Triton X-100/pH 8.2 buffer containing 10$^{10}$ beads Avidin-PB/BA-C$_{18}$ and 2.5×10$^{11}$ beads AbF-PB/nC$_{10}$ was added in each tube and the incubation was continued for additional 30 minutes by shaking in the dark at room temperature. Finally, each tube was illuminated for one minute using a halogen lamp fitted with a 650 nm cut off filter as light source, and then the chemiluminescent light was measured by integration for 20 sec using a Turner 20e luminometer. The results are summarized in FIG. 1.

EXAMPLE 2

Assay for Digoxin

Preparation of $Ab_{Dig}$-Biotin

Anti-digoxin monoclonal antibodies ($Ab_{Dig}$) were prepared according to standard hybrid cell line technology and antibodies were purified by immobilized Protein A. Then the $Ab_{Dig}$-biotin was prepared by mixing the antibody (about 2–2.5 mg/mL in 0.05M NaPi, 0.05M NaCl/pH 7.8) and biotin-LC$_7$-NHS (Pierce Chemical Co., Rockford, Ill.) (first solubilized in DMF and a small aliquot used for the reaction) together and incubating for three hours at 4° C. In the reaction mixture, the molar ratio of the reactants was antibody:Biotin-LC$_7$-NHS=1:25. The uncoupled biotin was removed by Sephadex® G-25 column. The final conjugate was stored in 0.05M NaPi, 0.001% Thimerosal/pH=7.4 at 4° C. or frozen.

II. Preparation of Dig-LC$_9$-F

This reagent was prepared in three successive steps by preparing (1) F-NHS, (2) F-LC$_9$-NH$_2$ and (3) Dig-LC$_9$-F.

A. Preparation of F-NHS. To 2 mL of 100 mg/mL 6-carboxyfluorescein and 30.6 mg/mL of NHS in DMF, 0.4 mL of 275 mg/mL DCC was added. The mixture was stirred overnight at room temperature in the dark. The formed dicyclohexylurea was removed by filtration. The formation of F-NHS was checked by TLC on silica plates, using $CH_2Cl_2$:methanol:acetic acid=85:15:1 solvent system. DMF was removed by rotovap, and the product (F-NHS) was dried further under reduced pressure and stored desiccated at 4° C.

B. Preparation of F-LC$_9$-NH$_2$. To 1.5 mL of a solution of bis-(3-aminopropyl)-methylamine (LC$_9$) (Aldrich Chemical Co., Milwaukee, Wis.) in DMF was added, 1.2 mL of 125 mg/mL F-NHS in DMF followed by incubation at room temperature overnight with stirring in the dark. The molar ratio of F-NHS:LC$_9$ was 1:40. Then, the reaction mixture was diluted 1/20 with 0.5M NaPi/pH 5.0, the pH of the mixture was adjusted to 5.0 by addition of phosphoric acid (1.0M) and the whole mixture was loaded onto a (2.5×10 cm) of BioRex-70® column, equilibrated in 0.5M NaPi/pH=5.0. After loading, the column was washed with the starting buffer until all of the bis-(3-aminopropyl) methyl amine was removed (monitored with TNBSA reaction). The column was washed with 0.001M NaPi/pH=6.0 to remove the 6-carboxyfluorescein contaminant. Washing with low ionic strength buffer removed not only the 6-carboxyfluorescein but also another fluorescein containing contaminant, which has not been identified. Then, the column was washed with D-H$_2$O to remove the salts. Finally, the column was stripped with 0.8M NH$_4$OH. The ammonium hydroxide was removed by lyophilization. After checking the purity, the product was stored desiccated at −20° C. The reaction was followed (and the purity of the product was checked) by paper electrophoresis (0.05M NaPi/pH=5.8, 20 minutes using the paragon electrophoresis system) and by TLC (C$_{18}$ plates, using 50% methanol in D-H$_2$O as solvent).

C. Preparation of Dig-LC$_9$-F. A solution containing 23.05 mg (0.05 mmoles) of Dig-CMO prepared as described in U.S. Pat. No. 4,039,385, Example 2, the disclosure of which is incorporated herein by reference, 50.35 mg (0.1 mmoles) F-LC$_9$-NH$_2$ and 19.2 mg (0.1 mmoles) EDAC in 1.5 mL of DMF/DMSO (5:1) solvent was stirred overnight at room temperature in the dark. The Dig-LC$_9$-F and Dig-CMO (if any left unreacted) were precipitated out by adding 3 mL of D-H$_2$O, filtered out, and the solvent discarded. The filtered material was resolubilized in a solvent system consisting of $CH_2Cl_2$:methanol:acetic acid=60:40:5 and was loaded onto a (1.5×20 cm) silica gel column in the same solvent system. Under these conditions, Dig-CMO moved ahead of Dig-LC$_9$-F conjugate, and the F-LC$_9$-NH$_2$ remained bound to the top of the column. The purity of the material was checked by TLC silica gel plates, using the solvent system described above, and by electrophoresis on paper at pH=5.8. The solvents were removed from the purified material by rotovap, and the product was resolubilized into a minimum volume of methanol/DMF (70:30) and then centrifuged to remove the insoluble materials (silica gel). The last step was performed to remove most of the silica gel, which may be solubilized and co-eluted with the product during the purification. The product was stored in methanol/DMF (70:30) solvent system at −10° C. to −20° C. The concentration of the product was determined by $A_{490}$ from a standard curve constructed using known amounts of 6-carboxyfluorescein.

III. Assay Protocol

The assay was performed by mixing 50 μl of digoxin calibrators in serum (human TSH free normal serum) with 50 μl of 1.74 ng/ml Digoxin-LC$_9$-F conjugate in assay buffer (0.05M Tris-HCl, 0.05M NaPi, 0.15M NaCl, 2 mg/ml BSA, 0.2 mg/ml BGG/pH 8.2) and 50 μl of 160 ng/ml $Ab_{Dig}$-biotin in the same buffer as above. These mixtures were incubated at room temperature for 15 minutes, then 0.75 ml of 0.05M Tris HCl, 0.05M NaPi, 0.15M NaCl/pH 8.2 buffer containing $10^{10}$ acceptor beads (Avidin-PB/BA-C$_{18}$) and $2.5×10^{11}$ sensitizing beads (Ab$_F$-PB/nC$_{10}$) was added in each tube and the incubation was continued for additional 30 minutes by shaking in dark at room temperature. Finally, each tube was illuminated for one minute using a halogen lamp fitted with 650 nm cut off filter as light source and then the chemiluminescent light was measured for 20 seconds integration using a Turner 20e luminometer. The results are summarized in FIG. 2.

EXAMPLE 3

Assay for Human Chorionic Gonadotropin and Assay for Thyroid stimulating Hormone

I. Reagents and Materials

A. The p-(N,N-dioctadecylcarboxamidomethoxy)-benzal acridan (BA-C$_{18}$) was synthesized by the following procedure:

All reagents were obtained from Aldrich Chemical Co., except as indicated.

1. p-Formylphenoxyacetic acid dioctadecylamide

To a 100 mL solution of freshly distilled tetrahydrofuran (THF) was added p-formylphenoxyacetic acid (K & K Labs) (MW 180, 0.540 g, 3.0 mmol), triethyl amine (MW 101.19, 0.333 g, 3.3 mmol) and trimethylacetyl chloride (MW 120.57, 0.398 g, 3.3 mmol). After 20 minutes of heating at reflux, dioctadecylamine (Fluke) (MW 522.01, 1.723 g, 3.3 mmol) was added. The reaction was refluxed overnight.

The following day, the reaction mixture was diluted with water and extracted from the reaction solution with methylene chloride. The methylene chloride extracts were dried over sodium sulfate.

2. p-(N,N-Dioctadecylcarboxamidomethoxy) benzal-9-methylacridan

To 10-dimethoxyphosphinyl-9-methyl acridan (Monatshi Chem. 114 3 (1988) (MW 303.27, 0.100 g, 3.3 mmol) in anhydrous THF was added 0.413 mL of 1.6M n-butyl lithium solution in hexane at −78° C. (acetone/dry ice bath) under argon. Upon the addition of the n-butyl lithium solution, the solution appeared yellow. A solution of the above amide in THF was added 20 minutes after the addition of n-butyl lithium. The reaction solution was permitted to warm to room temperature overnight.

The following day the product was isolated by TLC (Silica gel-3:7-ethylacetate/hexane). The isolated product was analyzed by mass spectrum analysis and NMR and stored in the dark.

B. Singlet oxygen generator dye ($nC_{10}$) was from ULTRA diagnostic Corporation. EDAC, SATA, hCG, and BSA were from Sigma Co. The $Ab_1(\alpha TSH)$-biotin and $Ab_2(\alpha HCG)$-biotin and the $Ab_2(\alpha TSH)$-F were prepared by procedures similar to those described in Example 1, paragraph II (see also U.S. patent application Ser. No. 07/389,659 filed Aug. 4, 1989, the relevant portions of which are incorporated herein by reference).

A luminometer from Turner Designs (model 20e) was sed.

II. Preparation of Oil Droplets Stabilized with anti-HCG Antibody ($Ab_1(\alpha HCG)$-OD/BA-$C_{18}$)

The anti-HCG antibody labeled oil droplets (OD) were prepared by transferring 1 ml of 10 mg/ml anti-HCG-$\beta$ (12A8, IgG) in a glass tube containing 50 μl of 5 mM dioctadecylbenzal acridan (BA-$C_{18}$) in dibutyl phthalate. The protein was in 0.05M NaPi, 0.15M NaCl/pH 7.6. The oil was emulsified by sonication and simultaneous continuous mechanical mixing. It should be noted that high energy sonicators were required for preparing smaller oil droplets. The sonication was performed for 7 minutes using Bronson sonicator (running water at room temperature was used as coolant). The unbound protein was removed by adding 25% $Na_2SO_4$ solution to get 8% to 9% final concentration and then centrifuging (microfuge, setting 8 for 10 min.). The washing step was performed three times (the centrifugation speed should be adjusted such that the oil droplets are separated but do not coalesce). After the final wash the particles were suspended in 1 ml of 0.05M NaPi, 0.15 NaCl, 4 mg/ml BSA/$pH_{7.6}$ and sonicated again for three minutes. The final volume of the preparation was adjusted to 5 ml and sucrose was added to 2% final concentration. These $Ab_1(\alpha HCG)$-OD/BA-$C_{18}$ particles were stored at 4° C. The Oil droplets prepared by the method described above were heterogenous in size with a average diameter of 1–5μ.

III. Preparation of Avidin-Lip/$nC_{10}$

The liposomes were prepared by methanol dilution method. Typically a mixture of lipids: Cholesterol (2.0 mg), DPPC (Avanti Polar Lipids, Alabaster, Ala.) (23.8), DPPG (Avanti Polar Lipids, Alabaster, Ala.) (6.5 mg), maleimide-DPPE (Molecular Probe, Eugene, Ore.) (0.5 mg) and $nC_{10}$ (0.5 mg were dissolved in warm methanol (200 μl) and then added into 2 ml of vortexing buffer-B (0.05 m NaPi, 0.05M NaCl, 5mM EDTA/pH 6.0). The suspension then was passed through a (1.5×20 cm) Sephadex G-25 column in buffer-B. The pooled liposome containing fractions were centrifuged by microfuge to remove any large particles, when necessary. Finally, the maleimide-containing liposomes were slowly added into stirred succinylated avidin-SH (prepared as described below) solution in buffer-B. After flushing with argon this mixture was mixed gently (no stirring bar) overnight at 4° C. The excess maleimide groups were blocked with 2 mM mercaptosuccinic acid (in reaction volume) for 30 min. at 4° C. followed by the addition of iodoacetic acid to a final 5 mM concentration to block the excess thiol groups (30 min at 4° C.). The reaction mixture was then concentrated to 2.5–3 ml by means of a Centriprep-30 ® device and the uncoupled avidin molecules were removed by gel filtration on a (1.5×50 cm) Sepharose-2B column in buffer-B.

IV. Preparation of Succinylated Avidin-SH

Avidin was reacted with SATA (5 moles per mole of avidin) (10 mg/ml avidin in 1M NaPi/$pH_{7.4}$) overnight at 4° C. To the same solution succinic anhydride in DMF (50 moles per mole of avidin) was added (total DMF was less than 1% of the reaction volume), and the solution was incubated for 2 hours. The pH of the reaction mixture w-as kept at 7.4 by addition of 0.5M $Na_2HPO_4$. The protected thiol groups (thioester) were liberated with hydroxylamine (0.1M, at pH 7.0) for 1 hour at room temperature. Finally, the excess small molecular weight molecules were removed by use of a 1.5×30 cm G-25 column in buffer-B (0.05M NaPi, 0.05M NaCl, 5 mM EDTA/$pH_{6.0}$, degased and argon saturated). The protein peak (avidin-SH) was collected and the protein was reacted with maleimide containing liposomes.

V. Preparation of Anti-Fluorescein coated $nC_{10}$-stained beads (AbF-PB/nC10

Carboxylated polystyrene beads (38 nm) (see Example 1, paragraph IIIB) were stained with $nC_{10}$. EDAC/-sulfo-NHS conjugation chemistry was used to couple the $Ab_F$ to these polystyrene beads. Typically, 10 ml of 0.02M NaPi containing 5 mg/ml $nC_{10}$ stained carboxylated polystyrene beads and 11 mg/ml sulfo-NHS (pH adjusted to 5.5) was mixed with 1 ml of freshly prepared solution of EDAC (200 mg/ml) in D-$H_2O$. After incubating at room temperature (in the dark) for 25 minutes, the beads were centrifuged to remove the excess EDAC (since EDAC causes microaggregation of these beads, it was possible to pellet them with conventional centrifuges, e.g., Sorval using SA-600 rotor at 15000 rpm). The pelleted beads were resuspended in 3 ml of 0.005M NaPi/$pH_{5.8}$ and then transferred into a stirred protein solution (15m of 0.02M Borax, 0.08M NaCl, 2 mg/ml 3G1 IgG (AbF), 8 mg/ml BSA/pH 8.9). The mixture was gently shaken (no stirring) overnight at 4° C. The remaining reactive groups on the beads, if any, were blocked with 0.083M glycine and 15 mg/ml BSA/$pH_{8.9}$ at 4° C. for 60 minutes. The uncoupled proteins were removed by successive washing with 0.05M NaPi, 0.15M NaCl/$pH_{7.6}$. The final pellet was resuspended in the washing buffer, sonicated, and stored as is at 4° C. The final size of these beads was 140 nm.

VI. Preparation of Avidin-Coated and Benzal Acridan-Stained beads (Avidin-PB/BA-C18)

Carboxylated latex beads (0.175μ) were stained with the BA-$C_{18}$. (See Example 1, paragraph IIIC.) EDAC/-sulfo-NHS conjugation chemistry was employed for conjugating the avidin to these particles. The activation of the beads by sulfo-NHS/EDAC was performed in the same way as it was described for AbF-PB/n$C_{10}$ preparation above. The activated beads (100 mg) were centrifuged to remove excess EDAC, then resuspended in 2.5 ml of 0.005M NaPi/pH 5.8 and transferred into a stirred avidin solution (15 ml of 0.025M Borax, 1.33 mg/ml avidin/p$H_{9.1}$). The mixture then was mixed gently at 4° C. overnight. The avidin on the beads was succinylated by adding 20 ul of 1M succinic anhydride in DMF (60-fold molar excess over avidin) and incubating further at 4° C. for 1 hour. The beads were blocked with 7 mg/ml BSA (the final concentration in the reaction mixture) for 60 min. at 4° C. Finally the beads were washed three times with 0.05M NaPi, 0.15M NaCl/p$H_{7.6}$ by centrifugation and stored in 10 ml of washing buffer. In the last step the beads were sonicated to obtain monodispersed particles. The size of the beads did not change significantly after protein labeling (~190 nm). The Avidin-PB/BA-$C_{18}$ was stored in washing buffer at 4° C.

VII. Preparation of Biotin-LC$_{21}$F

1. Reaction Scheme

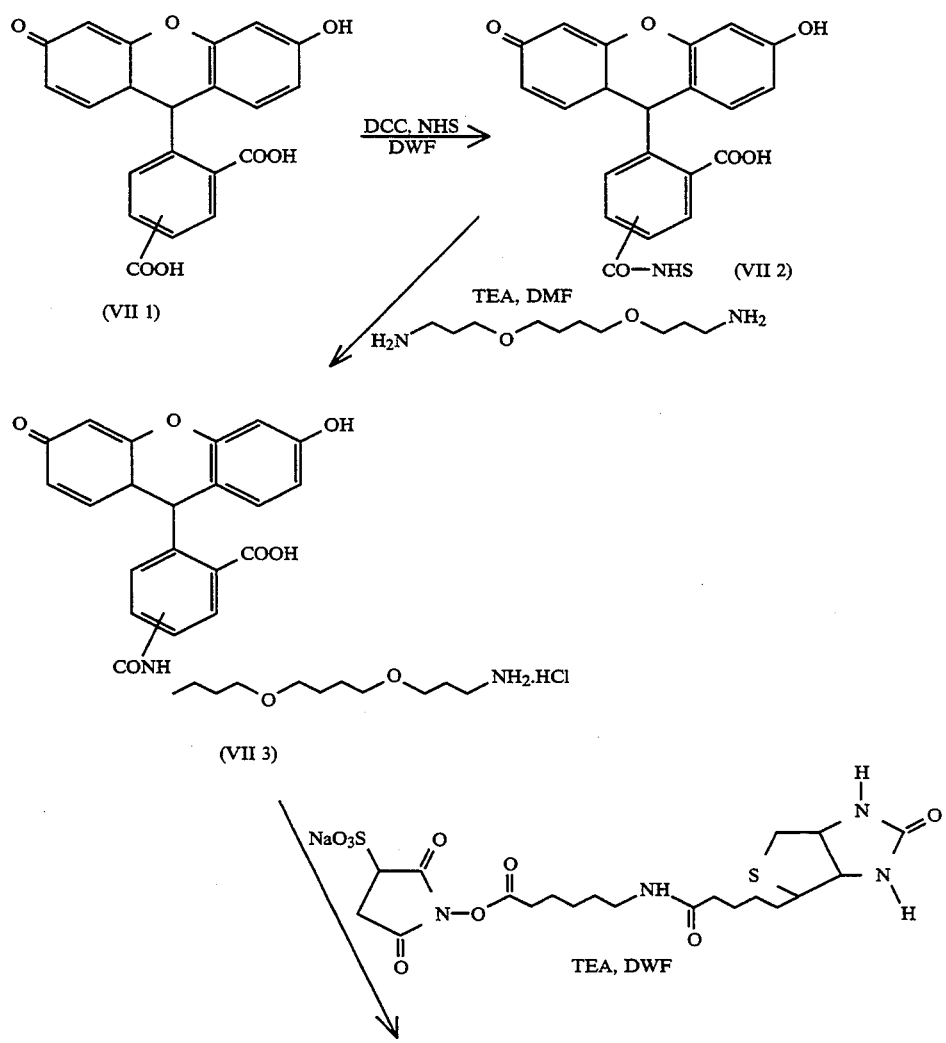

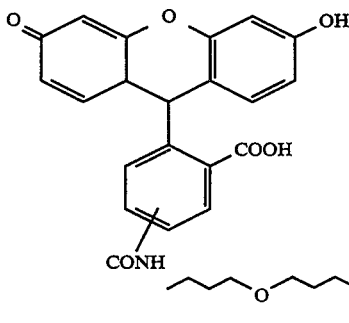
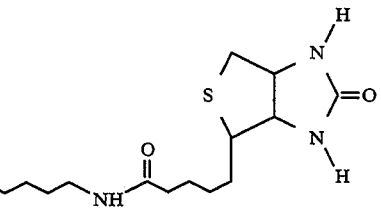

(VII 4)

2. Materials 6-carboxyfluorescein, Kodak; biotin-NHS ester, Pierce Chemical Co.; 4,9-dioxa-1,12-dodecane diamine, Aldrich Chemical Co.; dry DMF distilled from calcium oxide; Ag-MP-1 (Cl$^-$) anion exchange resin, BioRad Laboratories.

3. Fluorescein amine hydrochloride VII3

6-Carboxy fluorescein (VII 1) (10 g, 26.6 mmole) was dissolved in dry DMF (25 ml). N-hydroxysuccinimide (3.22 g, 28 mmole) was added as a solid to the DMF solution and allowed to dissolve. The mixture was then cooled in an ice bath. Dicyclohexyl carbodiimide (5.8 g, 28 mmole) was dissolved in dry DMF (10 ml) and added all at once to the cold DMF solution. The mixture was stirred at ice bath temperature for 30 min. and then allowed to come to room temperature. The course of the reaction was followed by tlc (10% MeOH-CH$_2$Cl$_2$ containing 1% acetic acid). After 3 hours, formation of the fluorescein NHS ester VII2 was complete.

4,9-Dioxa-1,12-dodecane diamine (25.5 g, 125 mmole) was diluted with dry DMF (10 ml). The fluorescein NHS ester reaction mixture was cooled in ice under an argon atmosphere and the diamine solution added dropwise over a period of 5 minutes. The cooling bath was removed and stirring was continued at room temperature. The course of the reaction was followed by tlc using the above system. When the reaction was judged complete, the mixture was diluted with water (100 ml) and cooled in ice to precipitate dicyclohexylurea which was removed by filtration.

The filtrate was slurried with AG-MP-1(Cl$^-$) anion exchange resin and poured into a chromatography column. The resin was washed with 50% aqueous methanol until free diamine could no longer be detected by ninhydrin. The resin was then eluted with 0.1 N hydrochloric acid in 50% aqueous methanol. Fluorescein amine hydrochloride eluted first followed by 6-carboxy-fluorescein. Pure fractions were pooled and taken to dryness on the rotovap. After drying under high vacuum 3.4g of pure fluorescein amine hydrochloride VII3 was recovered.

4. Fluorescein-LC$_{21}$-biotin VII 4

Fluorescein amine hydrochloride VII3 (350 mg, 0.61 mmole) was dissolved in dry DMF (15 ml). Triethylamine (300 μl) was added followed by biotin NHS ester (445 mg, 0.8 mmole). The course of the reaction was followed by tlc (MeOH-CH$_2$Cl$_2$-acetic acid-water, 20:78:1:1). When the reaction was judged complete, DMF was removed on the rotovap. The residue was dissolved in methanol (10 ml) and slurried with silica gel (10 g). The slurry was dried on the rotovap to a free flowing powder which was slurried in dichloromethane and applied to the top of a silica gel column (2.5×25 cm) equilibrated with dichloromethane. The column was eluted with the above tlc solvent mixture. Fractions containing product were pooled and solvent removed on the rotovap. The residue was taken up in ethanol and filtered. The filtrate was slowly evaporated and the product was deposited as a gum. The gum was dried under high vacuum to give 350 mg of fluorescein-LC$_{21}$-biotin VII 4 (F-LC$_{21}$-biotin) which was used without further characterization.

VIII. Assays

A. HCG assay standard curve (OD with Lip)

An HCG assay was performed by first mixing HCG (varying amounts), Ab$_1$(αHCG)-OD/BA-C$_{18}$ and Ab$_2$(αHCG)-biotin together. After incubation at room temperature for 1 hour, excess amount of Avidin-Lip/nC$_{10}$ was added and the incubation continued at room temperature for an additional 30 minutes. Finally, the tubes were illuminated for 1 minute each and the luminescence measured for 20 seconds.

Protocol

Combine: 50 μl of HCG at varying conc. in sample buffer, (0.05M NaPi, 0.15M NaCl, 0.04% BSA, 20% sucrose 4 mg/ml dextran sulfate (T-500) pH 7.5)

50 μl of 4 μg/ml Ab$_2$(αHcG)-biotin in assay buffer (0.05M NaPi, 0.15M NaCl, 0.4% BSA, pH 7.5), and 50 μl of Ab$_1$(αHCG)-OD/BA-C$_{18}$ reagent (5×10$^8$ OD/tube)

Incubate 1 hr at room temperature with shaking in the dark

Add:

50 μl of 1.5×10$^{12}$ Avidin-nC$_{10}$ Lip (7.3×10$^{10}$ lip/tube)

Incubate 30 min. at room temperature with shaking in the dark.

Illuminate for 1 min. with a halogen lamp (120 mW light output when using a 650 nm cut-off filter). Then, with light source off, measure emitted light intensity for 20 seconds. The results are summarized in FIG. 3.

B. Assay of Biotin-LC$_{21}$-F.

The test was performed by mixing 50 μL of avidin-PB/BA-C$_{18}$ (2×10$^{11}$ beads/ml), 50 μL of Ab$_F$-PB/nC$_{10}$(5×10$^{12}$beads/ml) and 100 μL of biotin-LC$_{21}$-F (varying amounts) in 0.05 NaPi, 0.15M NaCl, 4 mg/ml BSA/pH 7.6. This mixture was incubated at room temperature for 1.5 hours with shaking in the dark. Finally, each tube was illuminated with halogen lamp source (fitted with 650 nm cut off filter) for 1 minute after which the light output was measured for 20 seconds by integration of the light intensity in a Turner 20e luminometer. The results are summarized in FIG. 4.

C. TSH assay standard curve

The TSH assay was performed by mixing 200 μL of TSH at varying concentrations in 0.05 m NaPi, 0.15 m NaCl, 4 mg/ml BSA/pH 7.6 with 50 μL of 4 μg/ml $Ab_1$ (αTSH)-biotin and 4 μg/ml $Ab_2$(αTSH)-F. These mixtures were incubated at room temperature for 1.5 hours. Then, 100 μL of PBS containing $10^{10}$ Avidin-PB/BA-$C_{18}$ beads and $2.5 \times 10^{11}$ $Ab_F$-PB/$nC_{10}$ beads were added into each tube. The incubation was continued at room temperature for another 1.5 hours. Finally, each tube was illuminated with a halogen lamp source (fitted with 650 nm cut off filter) after which the light output was measured by integrating the light intensity for 20 seconds (FIG. 5 and FIG. 6) in a Turner 20e luminometer.

EXAMPLE 4

Assay for HCG using Soluble Photosensitizer and Acceptor Oil Droplets

Reagents

Acceptor dye stained oil droplets = $Ab_1$(αHCG)-OD/BA-$C_{18}$ (described in Example 3, Part II).

$Ab_2$(αHCG)-biotin - prepared similarly to Example 2, Part I, from the NHS derivative of biotin purchased from Pierce Chemical Co.

Strepavidin-T680 - from Ultralite Diagnosties Co., strepavidin labeled with water soluble analog of the $nC_{10}$ dye described above.

II. Assay

The assay was performed by mixing 50 μl of sample buffer (0.05M NaPi, 0.15M NaCl, 4 mg/ml BSA, 4 mg/ml Dextran-$SO_4$ (T500), 20% sucrose/pH 7.6) containing varying amounts of HCG with 50 μl of 4 μg/ml αHCG2-biotin in assay buffer (0.05M NaPi, 0.15M NaCl, 4 mg/ml BSA/pH 7.6) and 50 μl $Ab_1$(αHCG)-OD/BA-$C_{18}$ reagent containing $5 \times 10^8$ oil droplets. This mixture was incubated for one hour at room temperature in the dark. Then, 50 μl of 2 μg/ml Strepavidin-T680 in assay buffer was added in each tube and the incubation continued for additional 30 minutes. Finally, each tube was illuminated for 1 minute with a halogen lamp light source (fitted with 650 nm cut off filter) and then the light output was measured for 20 seconds using the Turner's 20e luminometer. The results are summarized in FIG. 7.

EXAMPLE 5

Homogeneous Assay for Target Oligonucleotide

The target sequence was selected from the *Escherichia coli* K12 DNAJ gene (J. C. A. Bardwell, K. Tilly, E Craig, J. King, M. Zylicz, and C. Georgopoulos, *J. Biol. Chem.* 261; 1782–1785 (1986)). A 50mer with the sequence shown was prepared by the phosphite triester approach using a Biosearch 8750, including a biotin incorporated at the 5'-end using Biotin-ON" Phosphoramidite (Clontech, Palo Alto, Calif.).

Sequence
GCGGGCGAAGGTGAAGCGGGCGAG-
CATGGCGCACCGGCAGGCGATCTGTA. The probe was a complementary 30mer including a fluorescein (F) attached to a modified C, having the sequence:

$$\overset{F}{\underset{|}{\text{CTGCCGGTGCGCCATGCTCGCCCGCTTCAC.}}}$$

The fluorescein was introduced by incorporating the modified nucleotide $N^4$-LCA-5-methyldeoxycytidine CED" Phosphoramidite (American Bionetics, Hayward, Calif.) and subsequently labeling with the N-hydroxysuccinimide ester of 5-carboxyfluorescein, using a 200-fold molar excess of ester in pH 9.0 $NaHCO_3$ containing 30% (v/v) DMF. The crude product was purified by polyacrylamide gel electrophoresis. Avidin-PB/BA-$C_{18}$ and $Ab_F$-PB/$nC_{10}$ beads were the same as described in earlier Examples.

A standard curve for the target was prepared by serially diluting it in 50 mM $NaH_2PO_4$, 600 mM NaCl, pH 7.5, containing 4 g/L bovine serum albumin and 10 mg/L calf thymus DNA as carriers. Aliquots (5 μL) were added to 4.8 pmoles of fluorescein-labeled probe in 5 μL of the same buffer in a 12×75 polypropylene test tube. The mixtures were covered and heated to 72° C. for 10 min to ensure complete hybridization. Approximately $10^{10}$ donor (sensitizer) ($Ab_F$-PB/$nC_{10}$) beads were added in 50 μL of 50 mM $NaH_2PO_4$, 600 mM NaCl, pH 7.5, containing 4 g/L bovine serum albumin, followed by $2.5 \times 10^{11}$ acceptor (Avidin-PB/BA-$C_{18}$) beads in 50 μL of the same. After 30 min at room temperature with shaking on an orbital shaker, each tube was illuminated for 1 min using a halogen lamp with a 650 nm filter as described in earlier Examples. Light generation was determined over 20 sec using a Turner luminometer. The resulting standard curve is shown in FIG. 8.

Although the foregoing invention has been described in some detail by way of illustration and example for purposes of clarity and understanding, it will be obvious that certain changes or modifications may be practiced within the scope of the appended claims.

What is claimed is:

1. A method for determining an analyte, said method comprising:
   providing in combination (1) a medium suspected of containing said analyte, (2) a label reagent comprising a first specific binding pair (sbp) member associated with a photochemically activatable chemiluminescent compound (PACC) wherein said first sbp member is capable of binding to said analyte or to a second sbp member to form a complex related to the presence of said analyte,
   photochemically activating said PACC, and
   detecting the amount of luminescence generated by said PACC, the amount thereof being related to the amount of analyte in said medium.

2. The method of claim 1 which is a homogenous method and wherein said photochemical activation comprises irradiation of said medium with light.

3. The method of claim 1 which is a heterogenous method and wherein said photochemical activation comprises excitation of said PACC with light.

4. The method of claim 1 wherein said photochemical activation comprises reaction of said PACC with singlet oxygen.

5. The method of claim 4 wherein said singlet oxygen is generated by activation of a photosensitizer.

6. The method of claim 5 wherein said photosensitizer is a dye.

7. The method of claim 1 wherein said detecting comprises detecting said luminescence directly.

8. The method of claim 1 wherein said detecting comprises employing a fluorescent energy acceptor.

9. The method of claim 8 wherein said fluorescent energy acceptor is bound to, or is capable of becoming bound to, an sbp member other than that of said label reagent.

10. The method of claim 1 wherein a surface is employed and an energy acceptor is employed that is bound to, or is capable of becoming bound to, said surface.

11. The method of claim 1 wherein said analyte and said first sbp member are each independently selected from the group consisting of ligands, receptors, and polynucleotides.

12. The method of claim 1 wherein said PACC contains an olefin group and one or more electron donating substituents in conjugation with said olefin group.

13. The method of claim 1 wherein said PACC is selected from the group consisting of 9-alkylidene acridans, enol ethers, 9-alkylidene xanthanes and enamines.

14. The method of claim 1 wherein said analyte is a polynucleotide.

15. The method of claim 1 wherein said first sbp member is an antibody.

16. The method of claim 1 wherein said second sbp member is analogous to said analyte.

17. The method of claim 1 wherein said second sbp member is analogous to or complementary to said analyte or to a third sbp member.

18. The method of claim 17 wherein said third sbp member is bound to a support.

19. The method of claim 1 wherein said complex becomes bound to a support.

20. The method of claim 1 wherein said second sbp member is bound to a support.

21. A method for determining an analyte, said method comprising:
   combining in an assay medium (1) a medium suspected of containing an analyte, and (2) a label reagent comprising a member of a specific binding pair (sbp member) bound to a photochemically activatable chemiluminescent compound (PACC) under conditions wherein an sbp member complex involving said label reagent is formed in relation to the presence of analyte in said medium,
   irradiating said assay medium with light to activate said PACC, and
   examining said assay medium for a signal, the presence or intensity thereof being related to the amount of analyte in said medium.

22. The method of claim 21 wherein an energy acceptor is included in said medium and energy from said PACC is capable of activating said energy acceptor.

23. The method of claim 21 wherein said medium is irradiated with light having a wavelength between 500 nm and 950 nm.

24. The method of claim 21 wherein said assay medium comprises a second sbp member other than said analyte.

25. The method of claim 21 wherein said energy acceptor is fluorescent.

26. The method of claim 25 wherein said fluorescent energy acceptor is bound to, or is capable of becoming bound to, a second sbp member or to a surface included in said medium.

27. The method of claim 21 wherein said analyte and said sbp member are each independently selected from the group consisting of ligands, receptors, and polynucleotides.

28. The method of claim 21 wherein said PACC contains an olefin group and one or more electron donating substituents in conjugation with said olefin group.

29. The method of claim 21 wherein said PACC is selected from the group consisting of 9-alkylidene acridans, enol ethers, 9-alkylidene xanthanes and enamines.

30. The method of claim 21 wherein said sbp member is complementary to said analyte.

31. The method of claim 21 wherein said assay medium comprises a second sbp member complementary to said analyte.

32. The method of claim 31 wherein said second sbp member is bound to, or is capable of becoming bound to, a support and said support is combined with said assay medium prior to, simultaneously with, or subsequent to the addition of said label reagent.

33. The method of claim 21 wherein said sbp member is analogous to said analyte and said assay medium comprises a second sbp member complementary to said analyte and said sbp member.

34. The method of claim 33 wherein said second sbp member is bound to a support.

35. The method of claim 21 wherein said sbp member is complementary to a second sbp member complementary to said analyte and said assay medium comprises said second sbp member.

36. The method of claim 35 wherein said second sbp member is bound to a support.

37. The method of claim 21 wherein said second sbp member is analogous to or complementary to said analyte or to a third sbp member.

38. The method of claim 37 wherein said third sbp member is bound to a support and said support is combined with said assay medium prior to, simultaneously with, or subsequent to the addition of said label reagent.

39. A method for determining an analyte, said method comprising:
   combining in an assay medium either simultaneously or wholly or partially sequentially (1) a medium suspected of containing an analyte, (2) a label reagent comprising a first member of a specific binding pair (sbp member) bound to a compound capable of chemiluminescence upon reaction with singlet oxygen ("said compound"), and (3) an insolubilized reagent comprising a second sbp member under conditions wherein an sbp member complex involving said label reagent and said insolubilized reagent is formed in relation to the presence of analyte in said medium,
   separating said assay medium and said insolubilized reagent,
   activating said compound in said medium or on said insolubilized reagent with light, and
   examining said assay medium or said reagent for a signal, the presence or intensity thereof being related to the amount of analyte in said medium.

40. The method of claim 39 wherein said assay medium is irradiated with light of wavelength between 500 and 950 nm to activate said compound.

41. The method of claim 39 wherein said singlet oxygen is generated by irradiation of a dye.

42. The method of claim 41 wherein said dye is selected from the group consisting of methylene blue, rose bengal, porphyrins, and phthalocyanines.

43. The method of claim 39 wherein said analyte and said sbp members are each independently selected from the group consisting of ligands, receptors, and polynucleotides.

44. The method of claim 39 wherein said compound contains an olefin group and one or more electron donating substituents in conjugation with said olefin group.

45. The method of claim 39 wherein said compound is selected from the group consisting of 9-alkylidene acridans, enol ethers, 9-alkylidene xanthanes and enamines.

46. The method of claim 39 wherein said first sbp member is complementary to said analyte.

47. The method of claim 39 wherein said a second sbp member is complementary to said analyte.

48. The method of claim 39 wherein said first sbp member is analogous to said analyte and said second sbp member is complementary to said analyte and said first sbp member.

49. The method of claim 39 wherein said singlet oxygen is generated by irradiating said assay medium with light of wavelength of from 450–950 nm.

50. A method for determining an analyte, said method comprising:
   combining in an assay medium either simultaneously or wholly or partially sequentially (1) a medium suspected of containing an analyte, (2) a label reagent comprising a first member of a specific binding pair (sbp member) bound to a compound capable of chemiluminescence upon reaction with singlet oxygen ("said compound"), (3) a singlet oxygen generator, and (4) a reagent comprising a fluorescent energy acceptor bound to, or capable of becoming bound to, a second sbp member, under conditions wherein an sbp member complex involving said label reagent and said energy acceptor is formed in relation to the presence of analyte in said medium and energy from said compound is capable of activating said fluorescent energy acceptor, activating said singlet oxygen generator, and examining said assay medium for a signal, the presence or intensity thereof being related to the amount of analyte in said medium.

51. The method of claim 50 wherein said singlet oxygen generator is a dye.

52. The method of claim 51 wherein said dye is selected from the group consisting of methylene blue, rose bengal, porphyrins, and phthalocyanines.

53. The method of claim 50 wherein said analyte and said sbp members are each independently selected from the group consisting of ligands, receptors, and polynucleotides.

54. The method of claim 50 wherein said chemiluminescent compound contains an olefin group and one or more electron donating substituents in conjugation with said olefin group.

55. The method of claim 50 wherein said compound is selected from the group consisting of 9-alkylidene acridans, enol ethers, 9-alkylidene xanthanes and enamines.

56. The method of claim 50 wherein said first sbp member is complementary to said analyte.

57. The method of claim 50 wherein said a second sbp member is complementary to said analyte.

58. The method of claim 50 wherein said first sbp is analogous to said analyte and said second sbp member is complementary to said analyte and said first sbp member.

59. The method of claim 50 wherein said singlet oxygen generator is activated by irradiating said assay medium with light of wavelength of from 450-950 nm.

60. A method for determining a polynucleotide analyte, said method comprising:

combining in an assay medium, (1) a sample suspected of containing a polynucleotide analyte and (2) a label reagent comprising a photochemically activatable chemiluminescent compound (PACC) bound to a polynucleotide, at least a portion of which is capable of hybridizing with said polynucleotide analyte, under conditions wherein said label reagent hybridizes with said polynucleotide analyte if present, irradiating said assay medium to activate said PACC, and measuring the fluorescent energy emitted from said medium, the amount thereof being related to the amount of analyte in said sample.

61. The method of claim 60 wherein said assay medium also includes a fluorescent compound capable of activation by said PACC.

62. The method of claim 61 wherein said fluorescent compound is capable of binding to a polynucleotide.

63. The method of claim 61 wherein said fluorescent compound is bound to a polynucleotide, at least a portion of which is capable of hybridizing with said polynucleotide analyte at a region other than that with which said label reagent hybridizes.

64. The method of claim 61 wherein said fluorescent compound is selected from the group consisting of coumarins and xanthene dyes.

65. The method of claim 60 wherein said PACC contains an olefin group and one or more electron donating substituents in conjugation with said olefin group.

66. The method of claim 60 wherein said PACC is selected from the group consisting of 9-alkylidene acridans, enol ethers, 9-alkylidene xanthanes and enamines.

67. The method of claim 60 wherein said medium is irradiated with light having wavelengths between 450 and 950 nm to activate said PACC.

68. The method of claim 60 wherein said medium comprises a dye capable in the excited state of activating molecular oxygen to singlet oxygen.

69. The method of claim 68 wherein said medium is irradiated with light of wavelength 450-950 nm to excite said dye.

70. The method of claim 60 wherein said polynucleotide analyte is DNA or RNA.

71. The method of claim 61 wherein said polynucleotide analyte is DNA or RNA.

72. A composition comprising a photochemically activated chemiluminescent compound (PACC) associated with a member of a specific binding pair.

73. The composition of claim 72 wherein said PACC contains an olefin group.

74. The composition of claim 72 wherein said PACC contains an olefin group and one or more electron donating substitutents in conjugation with said olefin group.

75. The composition of claim 72 wherein said PACC is selected from the group consisting of 9-alkyline-N-alkyl acridans, enolethers, enamines, and 9-alkylidene xanthenes.

76. The composition of claim 72 wherein said sbp member is selected from the group consisting of receptors, ligands, and polynucleotides.

77. A kit comprising in packaged combination: (1) a composition comprising a photochemically activatable chemiluminescent compound (PACC), having bound thereto a specific binding pair (sbp) member, and (2) a photosensitizer which is not in said composition.

78. The kit of claim 77 wherein said photosensitizer is a dye.

79. The kit of claim 78 wherein said dye is selected from the group consisting of methylene blue, rose bengal, porphyrins, and phthalocyanines.

80. The kit of claim 77 wherein said sbp member is selected from the group consisting of receptors, ligands, and polynucleotides.

81. The kit of claim 77 wherein said PACC contains an olefin group.

82. The kit of claim 77 wherein said PACC contains an olefin group and one or more electro donating substitutents in conjugation with said olefin group.

83. The kit of claim 77 wherein said PACC is selected from the group consisting of 9-alkylidene-N-alkyl acridans, enolethers, 9-alkylidene xanthenes and enamines.

84. The kit of claim 83 which comprises an energy acceptor.

85. The kit of claim 84 wherein said energy acceptor is bound to an sbp member.

86. The kit of claim 85 where said sbp member is selected from the group consisting of receptors, ligands, and polynucleotides.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear (ii) MOLECULE TYPE: DNA (genomic)T (iv) ANTI-SENSE: NO (v) FRAGMENT TYPE: internal (vi) ORIGINAL SOURCE:
  (A) ORGANISM: Escherichia coli
  (B) STRAIN: K12 DNAJ
  (C) INDIVIDUAL ISOLATE: Synthethic (xi) SEQUENCE DESCRIPTION: SEQ ID NO:1:

GCGGGCGAAG GTGAAGCGGG CGAGCATGGC GCACCGGCAG GCGATCTGTA  50

(2) INFORMATION FOR SEQ ID NO:2:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (v) FRAGMENT TYPE: internal (vi) ORIGINAL SOURCE:
    (A) ORGANISM: Escherichia coli
    (B) STRAIN: K12 DNAJ
    (C) INDIVIDUAL ISOLATE: Synthethic (xi) SEQUENCE DESCRIPTION: SEQ ID NO:2:

CTGCCGGTGC GCCATGCTCG CCCGCTTCAC  30